(12) United States Patent
Kannan et al.

(10) Patent No.: US 9,200,060 B2
(45) Date of Patent: Dec. 1, 2015

(54) MONOMERIC ANTIBODY FC

(75) Inventors: Gunasekaran Kannan, Westlake Village, CA (US); Hongxing Zhou, Bellevue, WA (US); Nancy Sun, Sammamish, WA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 13/511,133

(22) PCT Filed: Nov. 22, 2010

(86) PCT No.: PCT/US2010/057662
§ 371 (c)(1),
(2), (4) Date: May 21, 2012

(87) PCT Pub. No.: WO2011/063348
PCT Pub. Date: May 26, 2011

(65) Prior Publication Data
US 2012/0244578 A1   Sep. 27, 2012

Related U.S. Application Data

(60) Provisional application No. 61/263,730, filed on Nov. 23, 2009.

(51) Int. Cl.
*C07K 1/00* (2006.01)
*C07K 16/00* (2006.01)
*C12P 21/08* (2006.01)
*C07K 14/00* (2006.01)

(52) U.S. Cl.
CPC ............ *C07K 16/00* (2013.01); *C07K 2317/52* (2013.01)

(58) Field of Classification Search
None
See application file for complete search history.

(56) References Cited

U.S. PATENT DOCUMENTS

| 5,846,735 A | 12/1998 | Stapleton et al. | |
| 6,737,056 B1 * | 5/2004 | Presta | 424/133.1 |
| 2004/0110226 A1 * | 6/2004 | Lazar et al. | 435/7.1 |
| 2006/0074225 A1 * | 4/2006 | Chamberlain et al. | 530/387.1 |
| 2010/0136018 A1 | 6/2010 | Dolk et al. | |
| 2011/0054151 A1 * | 3/2011 | Lazar et al. | 530/389.2 |

FOREIGN PATENT DOCUMENTS

| WO | 2006/031994 A2 | 3/2006 |
| WO | 2006/104989 A2 | 10/2006 |
| WO | 2007/005612 A2 | 1/2007 |
| WO | 2009/089004 A1 | 7/2009 |
| WO | WO 2009/089004 | * 7/2009 |

OTHER PUBLICATIONS

Shinoda et al. PNAS 1981, 78;2:785-789.*
Ying et al., "Soluble monomeric IgG1 Fc," J Biol Chem 287:19399-19408, 2012.

* cited by examiner

*Primary Examiner* — Chun Dahle
(74) *Attorney, Agent, or Firm* — Jonathan M. Dermott

(57) ABSTRACT

The invention relates to monomeric Fc polypeptides and methods of making and using such polypeptides. The polypeptides comprise substitution of one or more hydrophobic interface residues in the CH3 region with a polar amino acid.

10 Claims, 13 Drawing Sheets

(a)

1. pTT5a-hG1fcCS-K392D,K409D-deltaH
2. pTT5a-hG1fcCS-K392D,K409D-deltaH-Y349T
3. pTT5a-hG1fcCS-K392D,K409D-deltaH-L351T
5. pTT5a-hG1fcCS-K392D,K409D-deltaH-L398T
6. pTT5a-hG1fcCS-K392D,K409D-deltaH-F405T
7. pTT5a-hG1fcCS-K392D,K409D-deltaH-Y407T
8. pTT5a-hG1fcCS-K392D,K409D-deltaH-F405T,Y407R
9. pTT5a-hG1fcCS-K392D,K409D-deltaH-Y407R (b)

SEQUENCE LISTING

```
<160> NUMBER OF SEQ ID NOS: 17

<210> SEQ ID NO 1
<211> LENGTH: 109
<212> TYPE: PRT
<213> ORGANISM: Human IgG1

<400> SEQUENCE: 1

Ala Lys Gly Gln Pro Arg Glu Pro Gln Val Tyr Thr Leu Pro Pro Ser
1               5                   10                  15

Arg Asp Glu Leu Thr Lys Asn Gln Val Ser Leu Thr Cys Leu Val Lys
            20                  25                  30

Gly Phe Tyr Pro Ser Asp Ile Ala Val Glu Trp Glu Ser Asn Gly Gln
        35                  40                  45

Pro Glu Asn Asn Tyr Lys Thr Thr Pro Pro Val Leu Asp Ser Asp Gly
    50                  55                  60

Ser Phe Phe Leu Tyr Ser Lys Leu Thr Val Asp Lys Ser Arg Trp Gln
65                  70                  75                  80
```

```
Gln Gly Asn Val Phe Ser Cys Ser Val Met His Glu Ala Leu His Asn
                85                  90                  95

His Tyr Thr Gln Lys Ser Leu Ser Leu Ser Pro Gly Lys
            100                 105

<210> SEQ ID NO 2
<211> LENGTH: 109
<212> TYPE: PRT
<213> ORGANISM: Human IgG2

<400> SEQUENCE: 2

Thr Lys Gly Gln Pro Arg Glu Pro Gln Val Tyr Thr Leu Pro Pro Ser
1               5                   10                  15

Arg Glu Glu Met Thr Lys Asn Gln Val Ser Leu Thr Cys Leu Val Lys
                20                  25                  30

Gly Phe Tyr Pro Ser Asp Ile Ala Val Glu Trp Glu Ser Asn Gly Gln
            35                  40                  45

Pro Glu Asn Asn Tyr Lys Thr Thr Pro Pro Met Leu Asp Ser Asp Gly
        50                  55                  60

Ser Phe Phe Leu Tyr Ser Lys Leu Thr Val Asp Lys Ser Arg Trp Gln
65                  70                  75                  80

Gln Gly Asn Val Phe Ser Cys Ser Val Met His Glu Ala Leu His Asn
                85                  90                  95

His Tyr Thr Gln Lys Ser Leu Ser Leu Ser Pro Gly Lys
            100                 105

<210> SEQ ID NO 3
<211> LENGTH: 109
<212> TYPE: PRT
<213> ORGANISM: Human IgG3

<400> SEQUENCE: 3

Thr Lys Gly Gln Pro Arg Glu Pro Gln Val Tyr Thr Leu Pro Pro Ser
1               5                   10                  15

Arg Glu Glu Met Thr Lys Asn Gln Val Ser Leu Thr Cys Leu Val Lys
                20                  25                  30

Gly Phe Tyr Pro Ser Asp Ile Ala Val Glu Trp Glu Ser Ser Gly Gln
            35                  40                  45

Pro Glu Asn Asn Tyr Asn Thr Thr Pro Pro Met Leu Asp Ser Asp Gly
        50                  55                  60

Ser Phe Phe Leu Tyr Ser Lys Leu Thr Val Asp Lys Ser Arg Trp Gln
65                  70                  75                  80

Gln Gly Asn Ile Phe Ser Cys Ser Val Met His Glu Ala Leu His Asn
                85                  90                  95

Arg Phe Thr Gln Lys Ser Leu Ser Leu Ser Pro Gly Lys
            100                 105

<210> SEQ ID NO 4
<211> LENGTH: 109
<212> TYPE: PRT
<213> ORGANISM: Human IgG4

<400> SEQUENCE: 4

Ala Lys Gly Gln Pro Arg Glu Pro Gln Val Tyr Thr Leu Pro Pro Ser
1               5                   10                  15

Gln Glu Glu Met Thr Lys Asn Gln Val Ser Leu Thr Cys Leu Val Lys
                20                  25                  30

Gly Phe Tyr Pro Ser Asp Ile Ala Val Glu Trp Glu Ser Asn Gly Gln
```

```
                35                  40                  45

Pro Glu Asn Asn Tyr Lys Thr Thr Pro Pro Val Leu Asp Ser Asp Gly
         50                  55                  60

Ser Phe Phe Leu Tyr Ser Arg Leu Thr Val Asp Lys Ser Arg Trp Gln
 65                  70                  75                  80

Glu Gly Asn Val Phe Ser Cys Ser Val Met His Glu Ala Leu His Asn
                 85                  90                  95

His Tyr Thr Gln Lys Ser Leu Ser Leu Ser Leu Gly Lys
            100                 105

<210> SEQ ID NO 5
<211> LENGTH: 106
<212> TYPE: PRT
<213> ORGANISM: Human IgG1

<400> SEQUENCE: 5

Ala Lys Gly Gln Pro Arg Glu Pro Gln Val Tyr Thr Leu Pro Pro Ser
 1               5                  10                  15

Arg Asp Glu Leu Thr Lys Asn Gln Val Ser Leu Thr Cys Leu Val Lys
             20                  25                  30

Gly Phe Tyr Pro Ser Asp Ile Ala Val Glu Trp Glu Ser Asn Gly Gln
         35                  40                  45

Pro Glu Asn Asn Tyr Lys Thr Thr Pro Pro Val Leu Asp Ser Asp Gly
         50                  55                  60

Ser Phe Phe Leu Tyr Ser Lys Leu Thr Val Asp Lys Ser Arg Trp Gln
 65                  70                  75                  80

Gln Gly Asn Val Phe Ser Cys Ser Val Met His Glu Ala Leu His Asn
                 85                  90                  95

His Tyr Thr Gln Lys Ser Leu Ser Leu Ser
            100                 105

<210> SEQ ID NO 6
<211> LENGTH: 106
<212> TYPE: PRT
<213> ORGANISM: Mouse IgG1

<400> SEQUENCE: 6

Thr Lys Gly Arg Pro Lys Ala Pro Gln Val Tyr Thr Ile Pro Pro Pro
 1               5                  10                  15

Lys Glu Gln Met Ala Lys Asp Lys Val Ser Leu Thr Cys Met Ile Thr
             20                  25                  30

Asp Phe Phe Pro Glu Asp Ile Thr Val Glu Trp Gln Trp Asn Gly Gln
         35                  40                  45

Pro Ala Glu Asn Tyr Lys Asn Thr Gln Pro Ile Met Asn Thr Asn Gly
         50                  55                  60

Ser Tyr Phe Val Tyr Ser Lys Leu Asn Val Gln Lys Ser Asn Trp Glu
 65                  70                  75                  80

Ala Gly Asn Thr Phe Thr Cys Ser Val Leu His Glu Gly Leu His Asn
                 85                  90                  95

His His Thr Glu Lys Ser Leu Ser His Ser
            100                 105

<210> SEQ ID NO 7
<211> LENGTH: 106
<212> TYPE: PRT
<213> ORGANISM: Mouse IgG2a

<400> SEQUENCE: 7
```

```
Pro Lys Gly Ser Val Arg Ala Pro Gln Val Tyr Val Leu Pro Pro
1               5                   10                  15

Glu Glu Glu Met Thr Lys Lys Gln Val Thr Leu Thr Cys Met Val Thr
                20                  25                  30

Asp Phe Met Pro Glu Asp Ile Tyr Val Glu Trp Thr Asn Asn Gly Lys
            35                  40                  45

Thr Glu Leu Asn Tyr Lys Asn Thr Glu Pro Val Leu Asp Ser Asp Gly
        50                  55                  60

Ser Tyr Phe Met Tyr Ser Lys Leu Arg Val Glu Lys Lys Asn Trp Val
65                  70                  75                  80

Glu Arg Asn Ser Tyr Ser Cys Ser Val Val His Glu Gly Leu His Asn
                85                  90                  95

His His Thr Thr Lys Ser Phe Ser Arg Thr
                100                 105
```

<210> SEQ ID NO 8
<211> LENGTH: 106
<212> TYPE: PRT
<213> ORGANISM: Mouse IgG2b

<400> SEQUENCE: 8

```
Ile Lys Gly Leu Val Arg Ala Pro Gln Val Tyr Thr Leu Pro Pro Pro
1               5                   10                  15

Ala Glu Gln Leu Ser Arg Lys Asp Val Ser Leu Thr Cys Leu Val Val
                20                  25                  30

Gly Phe Asn Pro Gly Asp Ile Ser Val Glu Trp Thr Ser Asn Gly His
            35                  40                  45

Thr Glu Glu Asn Tyr Lys Asp Thr Ala Pro Val Leu Asp Ser Asp Gly
        50                  55                  60

Ser Tyr Phe Ile Tyr Ser Lys Leu Asn Met Lys Thr Ser Lys Trp Glu
65                  70                  75                  80

Lys Thr Asp Ser Phe Ser Cys Asn Val Arg His Glu Gly Leu Lys Asn
                85                  90                  95

Tyr Tyr Leu Lys Lys Thr Ile Ser Arg Ser
                100                 105
```

<210> SEQ ID NO 9
<211> LENGTH: 106
<212> TYPE: PRT
<213> ORGANISM: Mouse IgG3

<400> SEQUENCE: 9

```
Pro Lys Gly Arg Ala Gln Thr Pro Gln Val Tyr Thr Ile Pro Pro Pro
1               5                   10                  15

Arg Glu Gln Met Ser Lys Lys Lys Val Ser Leu Thr Cys Leu Val Thr
                20                  25                  30

Asn Phe Phe Ser Glu Ala Ile Ser Val Glu Trp Glu Arg Asn Gly Glu
            35                  40                  45

Leu Glu Gln Asp Tyr Lys Asn Thr Pro Pro Ile Leu Asp Ser Asp Gly
        50                  55                  60

Thr Tyr Phe Leu Tyr Ser Lys Leu Thr Val Asp Thr Asp Ser Trp Leu
65                  70                  75                  80

Gln Gly Glu Ile Phe Thr Cys Ser Val Val His Glu Ala Leu His Asn
                85                  90                  95

His His Thr Gln Lys Asn Leu Ser Arg Ser
                100                 105
```

<210> SEQ ID NO 10
<211> LENGTH: 29
<212> TYPE: DNA
<213> ORGANISM: Artificial sequence
<220> FEATURE:
<223> OTHER INFORMATION: Oligo primer

<400> SEQUENCE: 10
gaaccacagg tgactaccct gcccccatc                                29

<210> SEQ ID NO 11
<211> LENGTH: 28
<212> TYPE: DNA
<213> ORGANISM: Artificial sequence
<220> FEATURE:
<223> OTHER INFORMATION: Oligo primer

<400> SEQUENCE: 11
caggtgtaca ccactccccc atcccggg                                 28

<210> SEQ ID NO 12
<211> LENGTH: 32
<212> TYPE: DNA
<213> ORGANISM: Artificial sequence
<220> FEATURE:
<223> OTHER INFORMATION: Oligo primer

<400> SEQUENCE: 12
cagcctgacc tgcactgtca aaggcttcta tc                            32

<210> SEQ ID NO 13
<211> LENGTH: 30
<212> TYPE: DNA
<213> ORGANISM: Artificial sequence
<220> FEATURE:
<223> OTHER INFORMATION: Oligo primer

<400> SEQUENCE: 13
cacgcctccc gtgactgact ccgacggctc                               30

<210> SEQ ID NO 14
<211> LENGTH: 27
<212> TYPE: DNA
<213> ORGANISM: Artificial sequence
<220> FEATURE:
<223> OTHER INFORMATION: Oligo primer

<400> SEQUENCE: 14
gacggctcct tcactctcta tagcgac                                  27

<210> SEQ ID NO 15
<211> LENGTH: 28
<212> TYPE: DNA
<213> ORGANISM: Artificial sequence
<220> FEATURE:
<223> OTHER INFORMATION: Oligo primer

<400> SEQUENCE: 15
ctccttcttc ctcactagcg acctcacc                                 28

<210> SEQ ID NO 16
<211> LENGTH: 33
<212> TYPE: DNA
<213> ORGANISM: Artificial sequence
<220> FEATURE:

```
<223> OTHER INFORMATION: Oligo primer

<400> SEQUENCE: 16
gacggctcct tcactctccg aagcgacctc acc                              33

<210> SEQ ID NO 17
<211> LENGTH: 28
<212> TYPE: DNA
<213> ORGANISM: Artificial sequence
<220> FEATURE:
<223> OTHER INFORMATION: Oligo primer

<400> SEQUENCE: 17
ctccttcttc ctccgaagcg acctcacc                                    28
```

MONOMERIC ANTIBODY FC

CROSS REFERENCE TO RELATED APPLICATIONS

This application is a National Stage application under 35 U.S.C. §371 of International Application No. PCT/US2010/057662 (which designated the United States), having an international filing date of Nov. 22, 2010, which claims priority to U.S. Provisional Patent Application No. 61/263,730, filed Nov. 23, 2009, which is incorporated herein by reference in its entirety.

REFERENCE TO THE SEQUENCE LISTING

The present application is being filed along with a Sequence Listing in electronic format. The Sequence Listing is provided as a file entitled A-1502-US-PCT_Seqlisting_ST25.txt, created May 21, 2012, which is 11 KB in size. The information in the electronic format of the Sequence Listing is incorporated herein by reference in its entirety.

BACKGROUND OF THE INVENTION

Antibodies play a central role in defense against invading non-self molecules. Antibodies' ability to interact with neonatal Fc-receptor (FcRn) in a pH-dependent manner confers them with extended serum half-life (Ghetie and Ward 2000). This unique feature of antibodies allows extending the half-life of therapeutic protein or peptide in the serum by engineering Fc-fusion molecules. Naturally occurring IgG antibodies and the engineered Fc-fusion molecules are bivalent and monospecific. This is due to the homodimeric nature of the Fc. For certain therapeutic applications, it would be desirable to retain all the positive attributes conferred by the antibody or the Fc fragment of the antibody, but achieve monovalent specificity by engineering monomeric Fc.

Antibodies belong to the immunoglobulin class of proteins which includes IgG, IgA, IgE, IgM, and IgD. The most abundant immunoglobulin class in human serum is IgG whose schematic structure is shown in the FIG. 1 (Deisenhofer 1981; Huber 1984; Roux 1999). The IgG structure has four chains, two light and two heavy chains; each light chain has two domains and each heavy chain has four domains. The antigen binding site is located in the Fab region (Fragment antigen binding) which contains a variable light (VL) and a variable heavy (VH) chain domain as well as constant light (LC) and constant heavy (CH1) chain domains. The Fc (Fragment crystallizable) fragment of the antibody contains CH2 and CH3 domain region of the heavy chain. The IgG molecule can be considered as a heterotetramer having two heavy chains that are held together by disulfide bonds (—S—S—) at the hinge region and two light chains. The number of hinge disulfide bonds varies among the immunoglobulin subclasses (Papadea and Check 1989). The FcRn binding site is located in the Fc region of the antibody (Martin, West et al. 2001), and thus the extended serum half-life property of the antibody is retained in the Fc fragment. The Fc region alone can be thought of as a homodimer of heavy chains comprising CH2 and CH3 domains.

SUMMARY OF THE INVENTION

Provided herein are Fc polypeptides containing alterations in the CH3 interface domain that significantly reduce the ability of the polypeptide to form homodimers. In preferred embodiments, the reduction in dimerization is around 100%. Preferably, the Fc polypeptides include one or more charged amino acid that is electrostatically unfavorable to CH3 homodimer formation and an amino acid substitution of one or more hydrophobic CH3 interface residues with a polar amino acid residue, e.g., threonine.

In certain embodiments, the CH3 domain is a human IgG CH3 domain having alterations that are electrostatically unfavorable to CH3 homodimer formation including a negatively charged amino acid, e.g., aspartic acid, at position 392 and/or position 409, and one or more substituted hydrophobic interface residues selected from the group consisting of Y349, L351, L368, V397, L398, F405, and Y407.

The monomeric Fc polypeptide may further comprise an antibody CH1 domain or is comprised within an antibody heavy chain. In certain embodiments, a monomeric antibody comprises the monomeric heavy chain and a light chain, essentially creating a half-antibody. The monomeric heavy chain may have one or more mutated cysteine residues to prevent disulfide bond formation. Particularly useful cysteine mutations are those in the hinge region of the heavy chain.

In one aspect of the invention, a polypeptide comprises an antibody CH3 domain having decreased ability to form homodimers compared to a polypeptide comprising a wild-type CH3 domain. Preferred polypeptides comprise a CH3 domain of an antibody wherein the CH3 domain comprises an amino acid sequence differing from a wild-type CH3 domain such that one or more charged amino acids are replaced with amino acids electrostatically unfavorable to CH3 homodimer formation, and one or more hydrophobic interface residues are replaced with a polar amino acid.

Other aspects of the invention are nucleic acids encoding monomeric Fc polypeptides, expression vectors comprising such nucleic acids, and host cells which contain such expression vectors.

Embodiments of the invention further include methods of preparing a monomeric Fc polypeptide. In preferred embodiments, such methods comprise culturing a host cell comprising a nucleic acid encoding a monomeric Fc polypeptide under conditions wherein the monomeric Fc polypeptide is expressed, and then recovering the monomeric Fc polypeptide from the host cell culture.

DETAILED DESCRIPTION OF PREFERRED EMBODIMENTS

The wild-type Fc is homodimeric in nature and this feature is driven by the strong, high-affinity interaction that exists between the two CH3 domains. Described herein are monomeric Fc molecules and methods of making and using such molecules. Although the term "Fc" is typically thought of as a homodimer of polypeptides, the term as used herein, due to the unique properties of the polypeptides of the invention, will also include monomeric polypeptides which comprise a sequence of amino acids corresponding to the Fc portion of the heavy chain, e.g., containing a CH2 and CH3 domain.

The methods described herein demonstrate that by substituting residues at the CH3 domain interface it is possible to completely disrupt CH3/CH3 association yet maintain stability of the molecule, thus achieving a monomeric Fc. The monomeric nature of the altered Fc can be assessed by e.g., Size Exclusion Chromatography (SEC) and Analytical Ultra Centrifugation (AUC). The substitutions accomplish two things—one is to hinder the homodimer formation of the CH3 domain and the other is to stabilize the monomeric form of Fc.

Methodology for identifying amino acids making up a CH3-CH3 interface is disclosed in WO2009089004. A total of 48 antibody crystal structures which had co-ordinates corresponding to the Fc region were identified from the Protein Data Bank (PDB) (Bernstein, Koetzle et al. 1977) using a structure based search algorithm (Ye and Godzik 2004). Examination of the identified Fc crystal structures revealed that the structure determined at highest resolution corresponds to the Fc fragment of RITUXIMAB bound to a minimized version of the B-domain from protein A called Z34C (PDB code: 1L6X). The biological Fc homodimer structure for 1L6X was generated using the deposited Fc monomer co-ordinates and crystal symmetry. Two methods were used to identify the residues involved in the CH3-CH3 domain interaction: (i) contact as determined by distance limit criterion and (ii) solvent accessible surface area analysis.

According to the contact based method, interface residues are defined as residues whose side chain heavy atoms are positioned closer than a specified limit from the heavy atoms of any residues in the second chain. Though 4.5 Å distance limit is preferred, one could also use longer distance limit (for example, 5.5 Å) in order to identify the interface residues (Bahar and Jernigan 1997).

Figure 3:
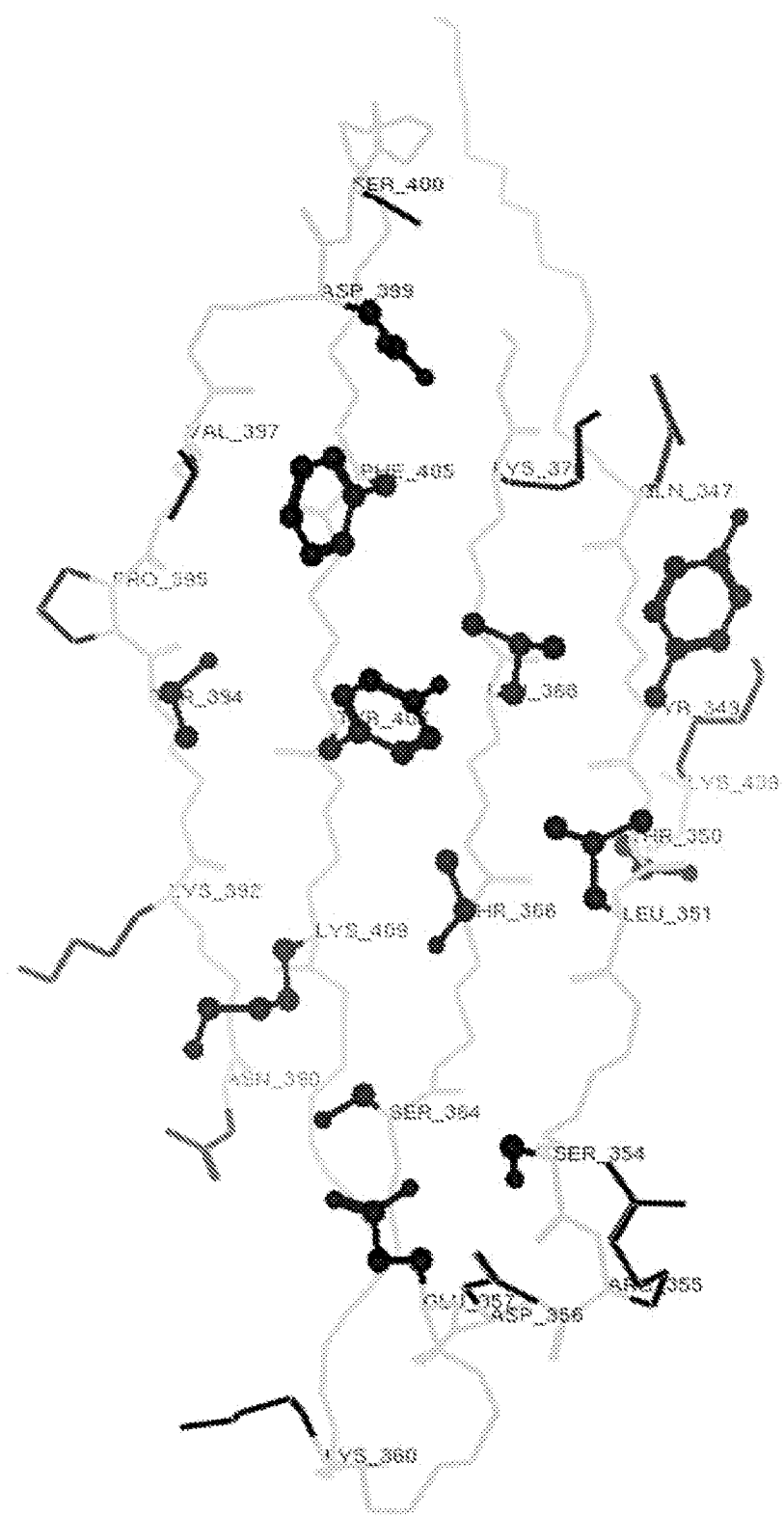
FIG. 3. CH3 domain interface structure with residues involved in the domain-domain interaction shown. The interface residues were identified using a distance cutoff method. Structurally conserved and buried (solvent accessible surface area≤10%) residues are shown in the ball-and-stick model. Solvent exposed or structurally not conserved residues are shown in the stick representation. The analysis is based on the IgG1 crystal structure (PDB code: 1L6X) which is determined at high-resolution (1.65 Å) (Idusogie, Presta et al. 2000).
Figure 4:
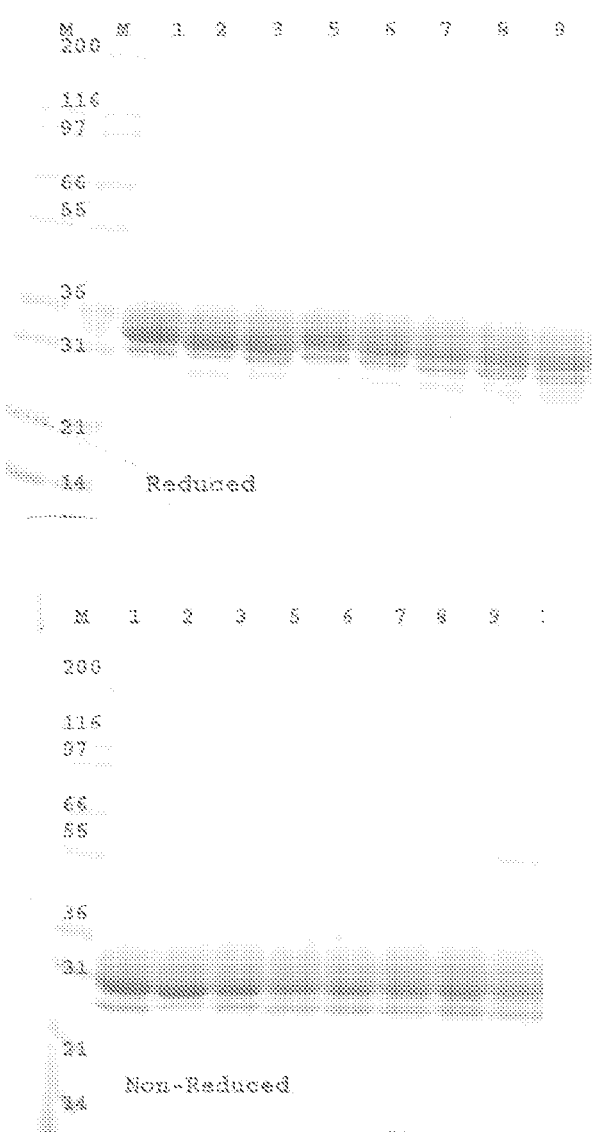
FIG. 4. (a) List of constructs designed with mutations in the CH3 domain interface of Fc and (b) SDS-PAGE coomassie gel stained with GELCODE™ Blue Staining Reagent for eight purified Fc mutant proteins. Mutant #4 of Table 2 was not included due to insufficient amount of protein. The constructs migrate similarly in the reduced and non-reduced gel due to the fact that these Fc constructs lack hinge disulfides. In other words, unlike IgG molecules, there are no inter-heavy chain disulfides connecting the two heavy chains since the goal here is to achieve monomeric Fc heavy chain.
Figure 5A:
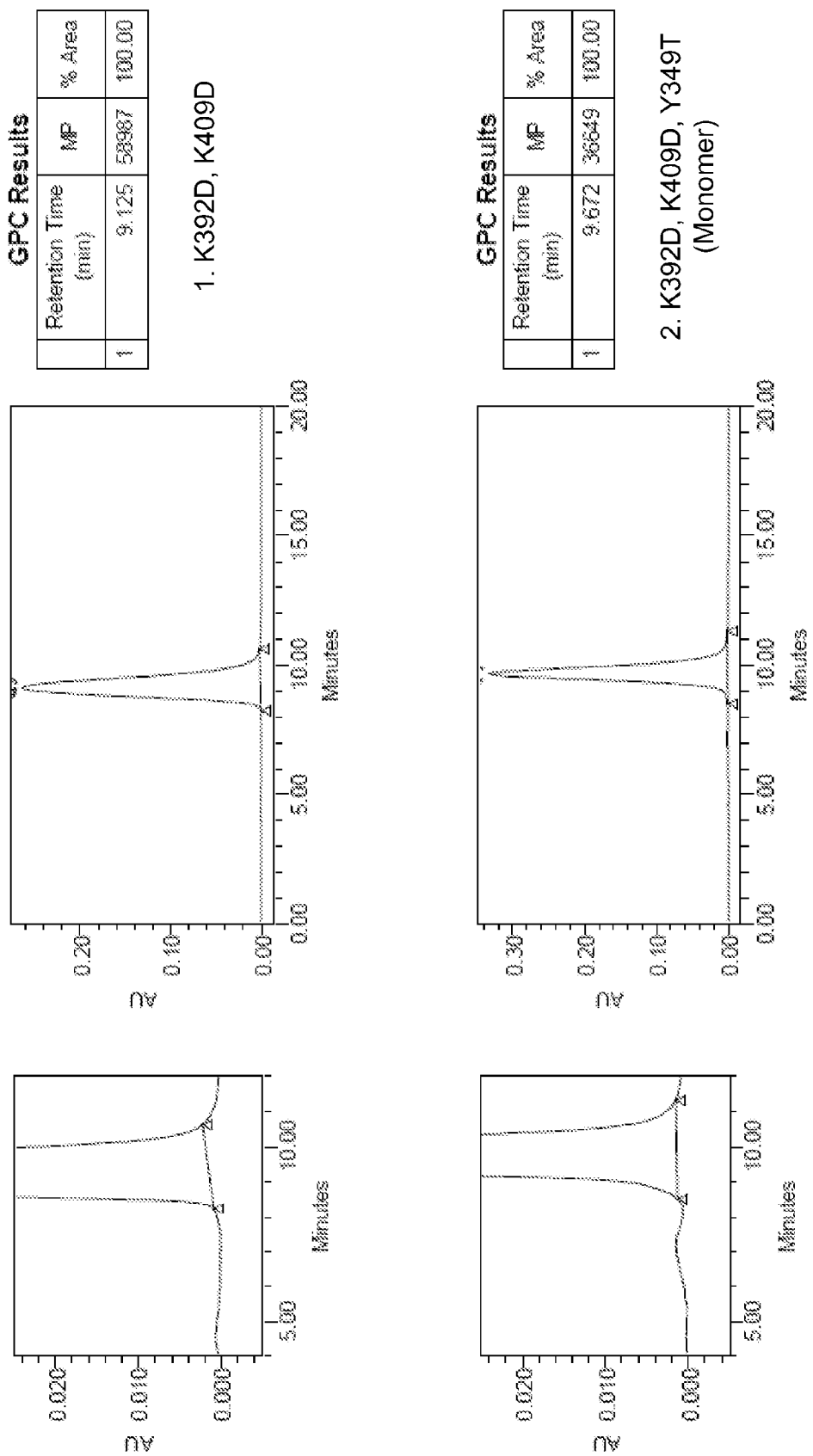
FIG. 5A-5E. Size Exclusion Chromatography (SEC) profiles for all the 9 constructs listed in Table 2. The constructs that show an exemplary monomeric SEC profile are labeled as 'Monomer'.
Figure 5B:
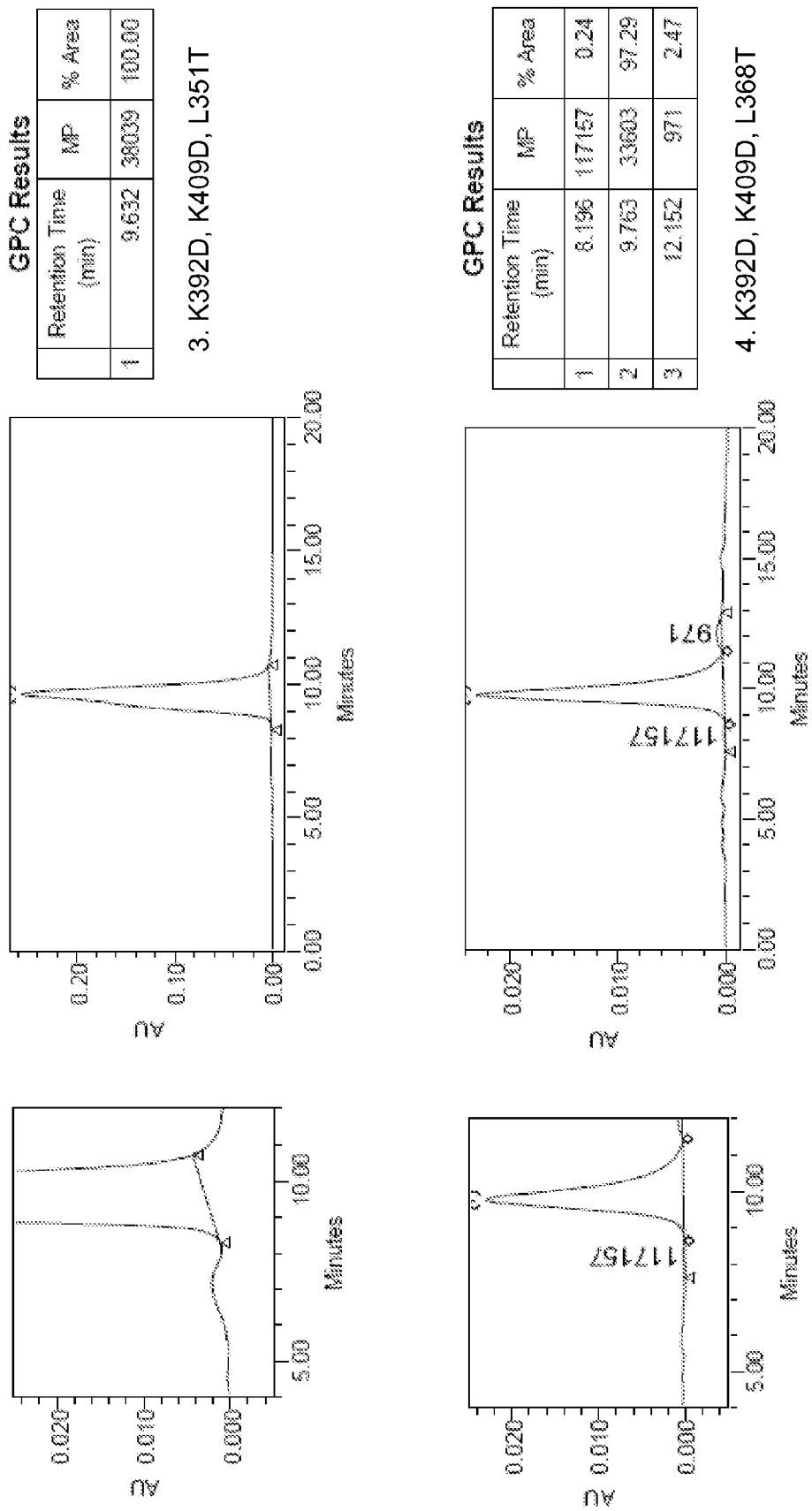
Figure 5C:
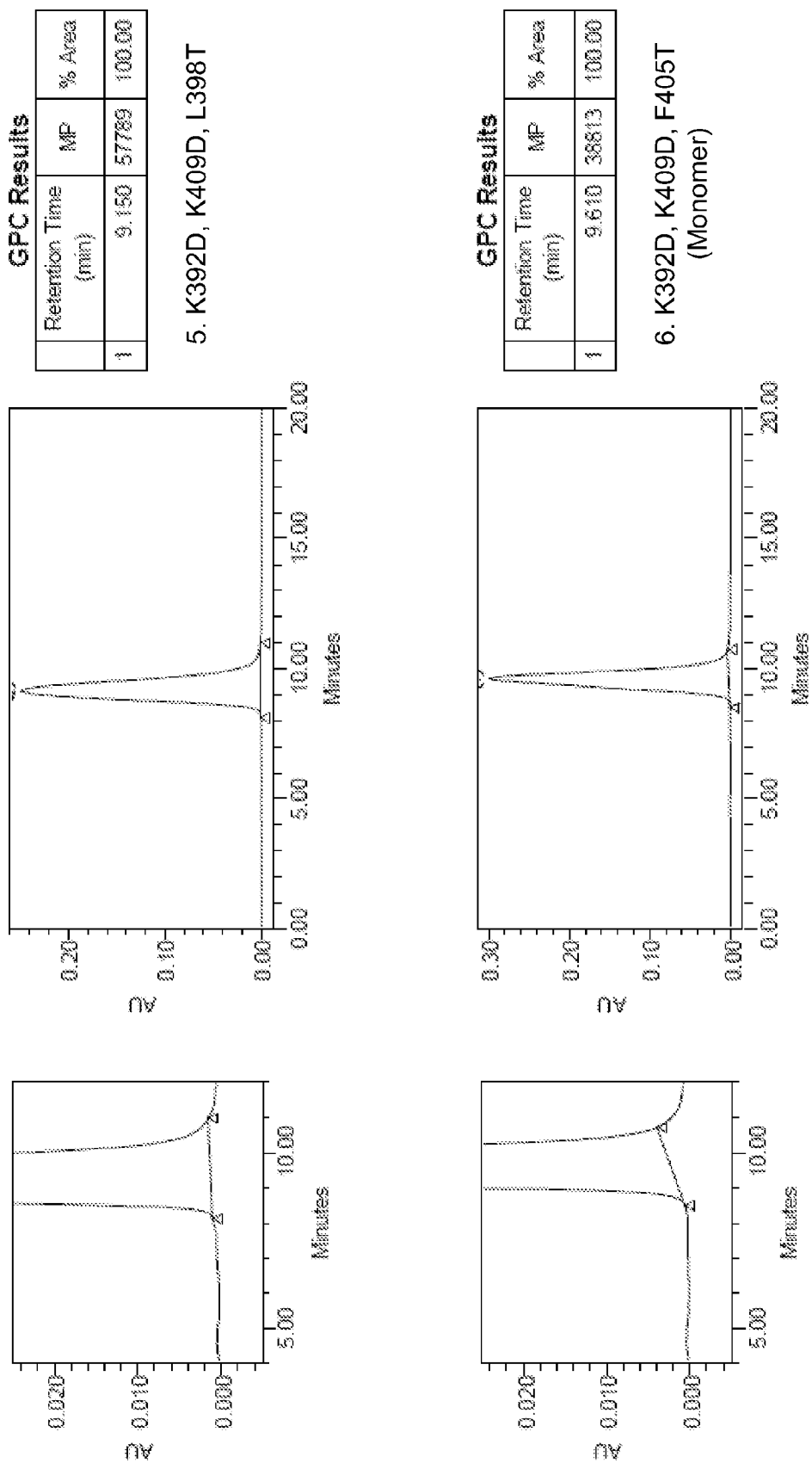
Figure 5D:
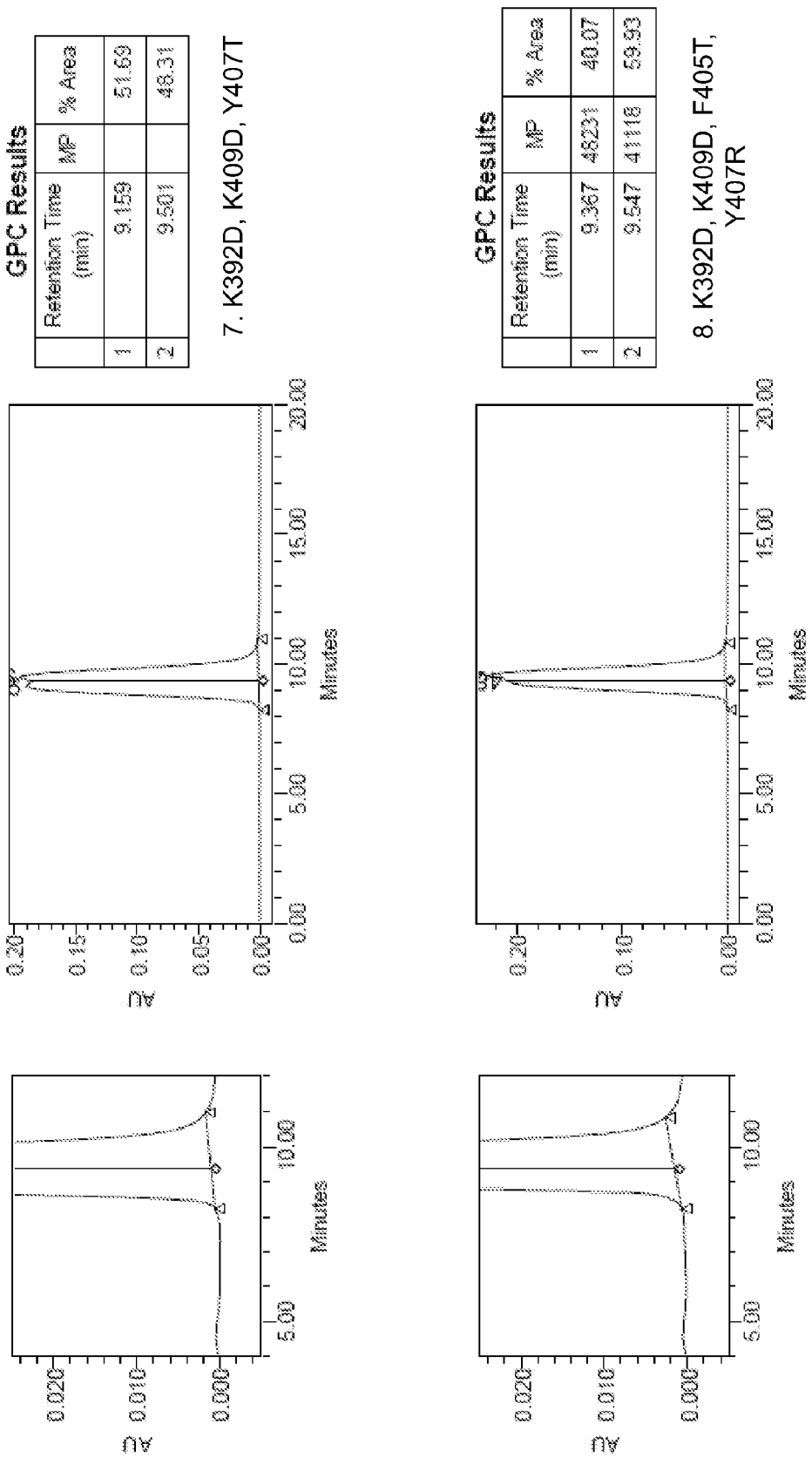
Figure 5E:
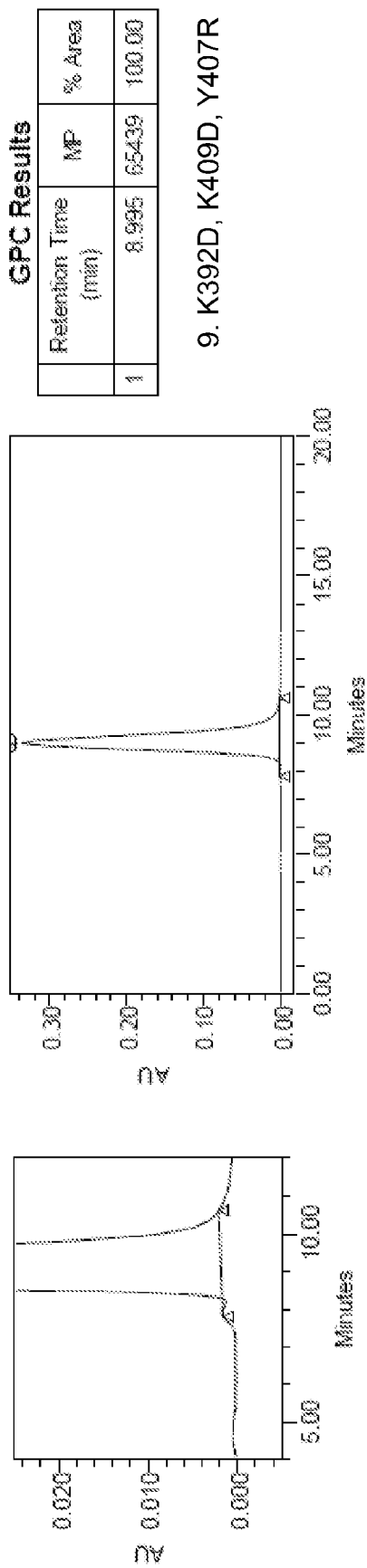
Figure 8:
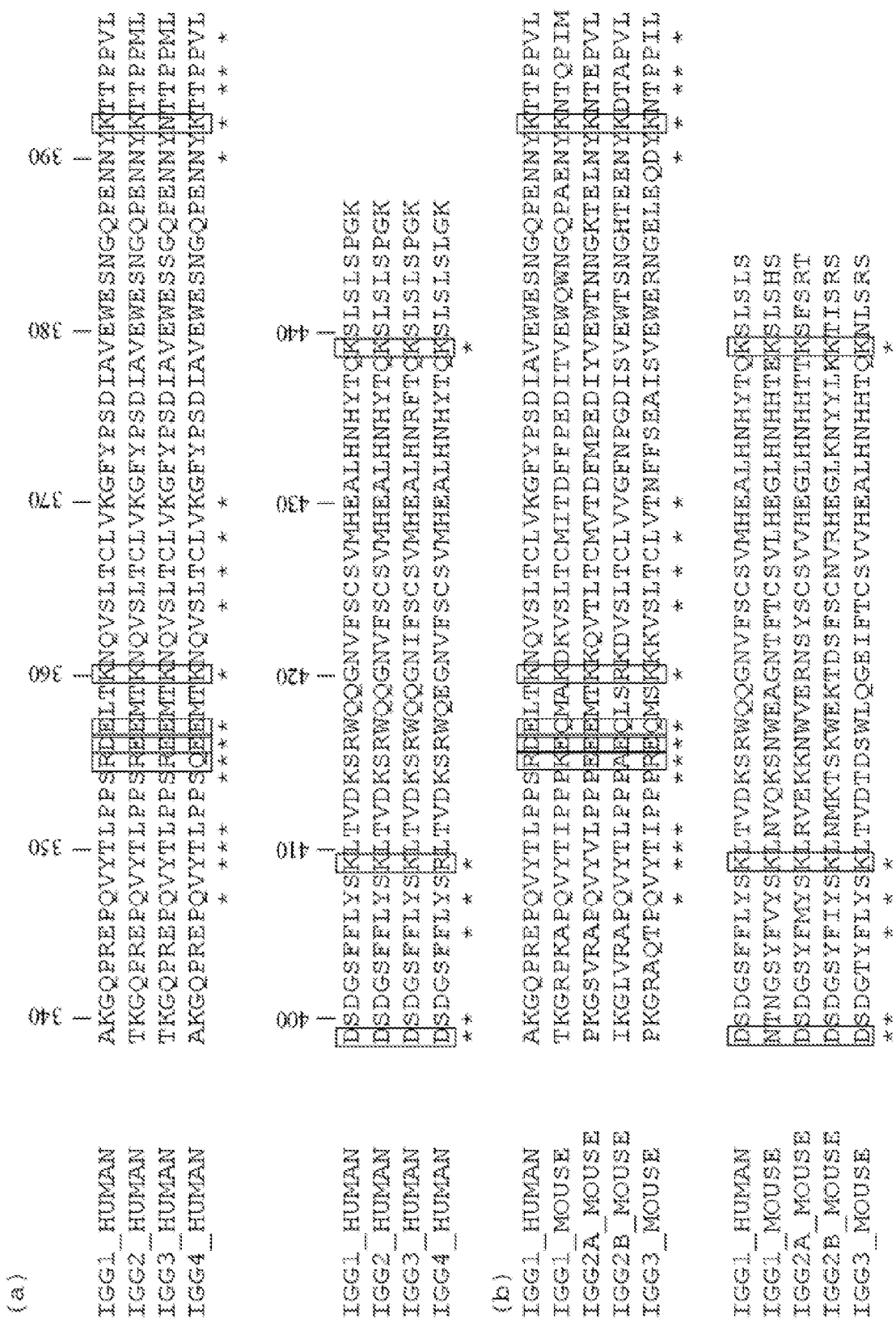
FIG. 8. Sequence comparison of CH3 domain of human and mouse IgG subclasses. The identified CH3 domain interface residues (24, Table 1; indicated by '*') are highly conserved. Therefore, the mutations that lead to monomerization in human IgG1 Fc can be extended to other human IgG subclasses as well as to species other than human. In (a), the sequences derived from human IgG1, IgG2, IgG3, and IgG4 correspond to SEQ ID NO:1, SEQ ID NO:2, SEQ ID NO:3, and SEQ ID NO:4, respectively. In (b), the sequences derived from human IgG1, mouse IgG1, mouse IgG2a, mouse IgG2b, and mouse IgG3 correspond to SEQ ID NO:5, SEQ ID NO:6, SEQ ID NO:7, SEQ ID NO:8, and SEQ ID NO:9, respectively.
Figure 9:
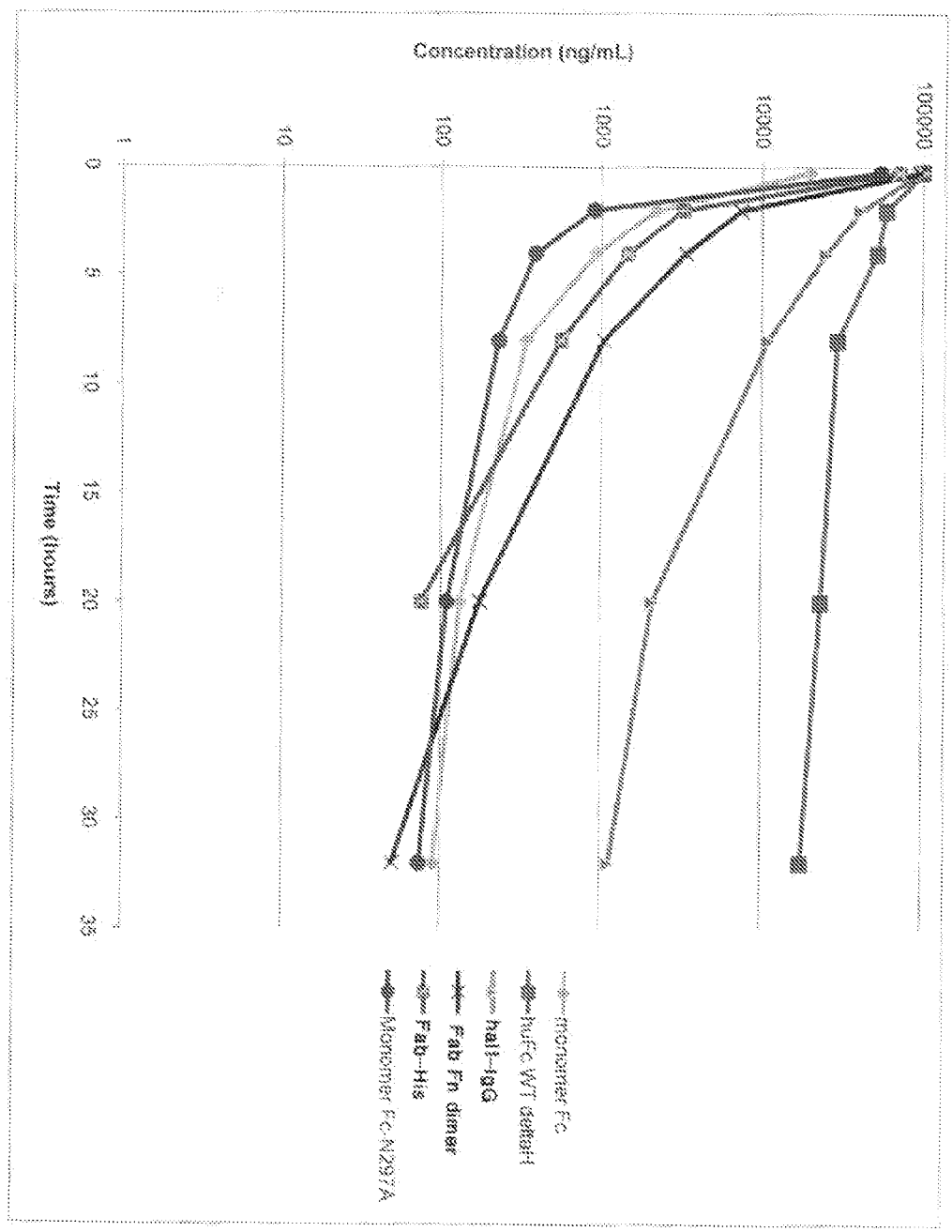
FIG. 9. The pharmacokinetics of various Fc fusion molecules in mice as described in Example 2.

Table 1 lists twenty four interface residues identified based on the contact criterion method, using the distance limit of 4.5 Å. These residues were further examined for structural conservation. For this purpose, 48 Fc crystal structures identified from the PDB were superimposed and analyzed by calculating root mean square deviation for the side chain heavy atoms. FIG. 3 shows the CH3 domain interface along with the structurally conserved, buried (% ASA≤10), and exposed (% ASA>10) positions (% ASA refers to ratio of observed ASA to the standard ASA of amino acids; (Lee and Richards 1971)). Conservation of interface residues among Human and Mouse IgG subclasses as well as among other Ig classes was also examined through sequence comparisons (FIG. 8).

Various substitutions or mutations to the Fc portion of an antibody are described herein. Such variations are designated by the amino acid at that position in the wild-type antibody heavy chain based on the EU numbering scheme of Kabat followed by the amino acid substituted into that position. For example, when the tyrosine at EU position 349 is substituted with threonine, it is designated "Y349T." By "wild-type sequence," it is meant a sequence of amino acids that occurs naturally within a species of animals, e.g., humans. Wild-type sequence may vary slightly between individuals within a population, e.g., different alleles for the various immunoglobulin chains are known in the art.

In order to discourage the homodimer formation, one or more residues that make up the CH3-CH3 interface are replaced with a charged amino acid such that the interaction becomes electrostatically unfavorable. In preferred embodiments, a positive-charged amino acid in the interface, such as lysine, arginine, or histidine, is replaced with a negative-charged amino acid, such as aspartic acid or glutamic acid, and/or a negative-charged amino acid in the interface is replaced with a positive charged amino acid. Using human IgG as an example, charged residues within the interface that may be changed to the opposing charge include R355, D356, E357, K370, K392, D399, K409, and K439. In certain preferred embodiments, two or more charged residues within the interface are changed to an opposite charge. Exemplary molecules include those comprising K392D and K409D mutations and those comprising D399K and D 356K mutations.

In order to maintain stability of the polypeptide in monomeric form, one or more large hydrophobic residues that make up the CH3-CH3 interface are replaced with a small polar amino acid. Using human IgG as an example, large hydrophobic residues of the CH3-CH3 interface include Y349, L351, L368, L398, V397, F405, and Y407. Small polar amino acid residues include asparagine, cysteine, glutamine, serine, and threonine.

In the Examples, two of the positively charged Lys residues that are closely located at the CH3 domain interface were mutated to Asp. Threonine scanning mutagenesis was then carried out on the structurally conserved large hydrophobic residues in the background of these two Lys to Asp mutations. Fc molecules comprising K392D K409D mutations along with the various substitutions with threonine were analyzed for monomer formation. Exemplary monomeric Fc molecules include those having K392D K409D Y349T substitutions and those having K392D K409D F405T substitutions.

Due to half-molecule nature of the Fc monomer, its thermal stability is lower than that of the Fc dimer which has high-affinity CH3-CH3 domain interaction. In order to increase thermal stability, one or more intra-domain disulfide bonds may be introduced in CH2 and CH3 domains. Disulfide bonds may be introduced by mutating one or more the following pairs of amino acids LYS246-ASP249
SER267-GLU269
THR393-SER408
PRO245-PRO257
PRO247-ASP376
ASP249-PRO257
VAL266-TYR300
ASP270-LYS326
LEU309-ASP312
ALA339-PRO374
PRO343-ALA431
ARG344-TYR373
THR350-LEU441
TRP381-GLU388
PRO396-PHE404
PHE241-VAL262
LEU242-LYS334
PHE243-THR260
PRO245-ASP249
LYS248-ALA378
ASP249-ARG255
THR250-PRO257
LEU251-HIS435
MET252-ARG255
VAL259-LEU306
CYS261-SER304
VAL263-VAL302
VAL264-ASP265
LYS274-SER324
ASN276-LYS322
TYR278-LYS320
ALA287-LEU306
LYS290-VAL303
ARG292-VAL302
ASP312-LYS317
SER324-PRO331
GLU345-ALA431
PRO346-PHE372
VAL348-LYS439
TYR349-LEU368
LEU351-THR366
PRO353-GLU357
PRO353-VAL363
SER354-ASP356
LEU365-LEU410
CYS367-SER408
LYS370-PHE405
SER375-PRO396
SER375-PHE404
ALA378-MET428
GLU380-SER426
TYR391-LEU410
VAL422-SER442
ASN434-TYR436

Figure 6:
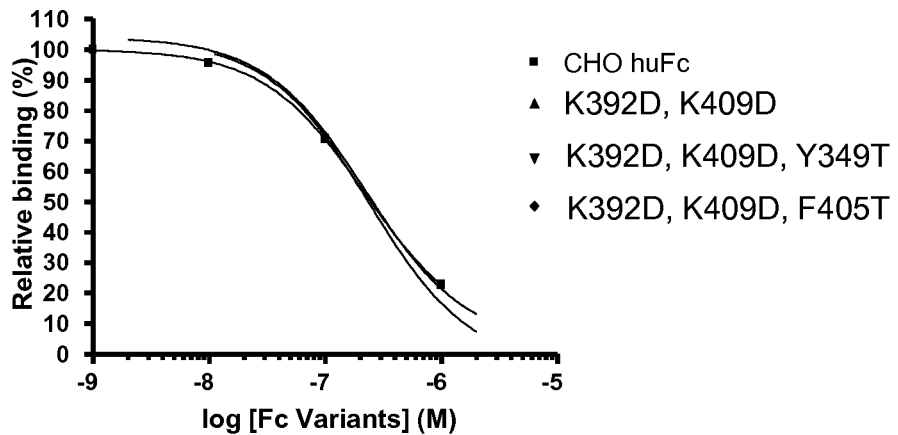
FIG. 6. BIACORE analysis of human and mouse FcRn binding to wild-type and mutant Fc constructs.
Figure 6:
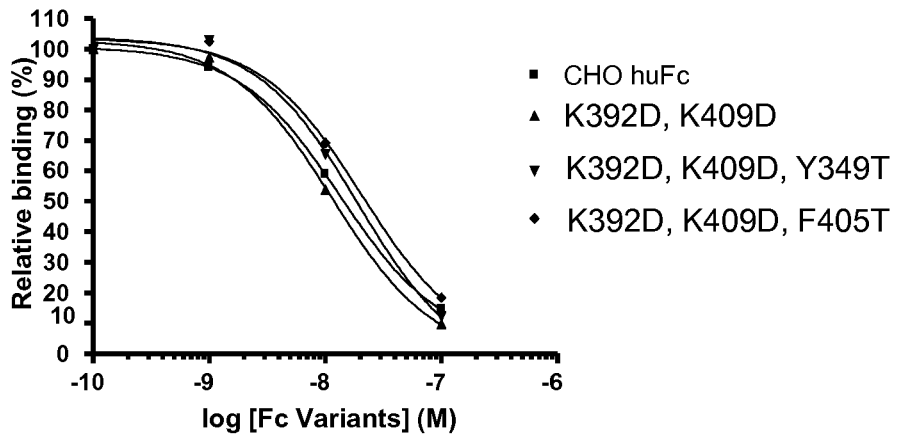
Figure 7:
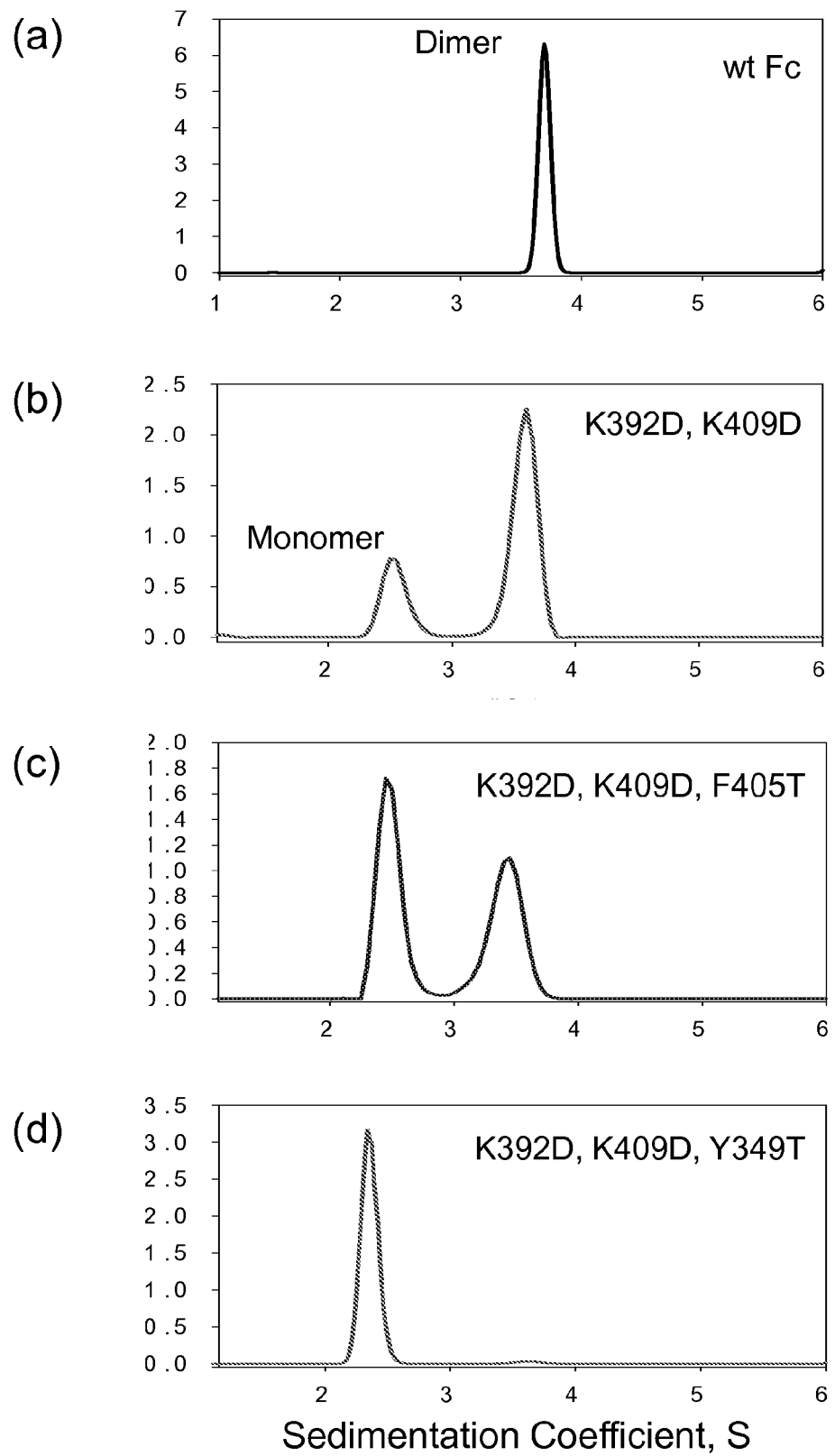
FIG. 7. Analysis of protein size using analytical ultracentrifugation (AUC).

An antibodies ability to interact with neonatal Fc-receptor (FcRn) in a pH dependent manner confers it with extended serum half-life. In preferred embodiments, monomeric Fc molecules of the present invention retain the ability to bind FcRn similarly if not superiorly to wild-type Fc polypeptides (FIG. 6). As shown in Example 2, the monomeric Fc molecules of the present invention can retain the extended serum half-life exhibited by antibodies and, thus, are useful for extending the serum half-life of the polypeptides covalently bound to, e.g. fused to, the monomeric Fc polypeptide. It is further contemplated that the monomeric Fc may be engineered to contain one or more further mutations that increase the affinity for FcRn, thereby further increasing the half-life of the molecule in circulation. Such further mutations include, but are not limited to, M252Y/S254T/T256E, M428L/N434S, T250Q/M428L, N434H, T307Q/N434A, T307Q/N434S, T307Q/E380A/N434S, and V308P/N434S.

The compositions and methods of the present invention are not limited to variants of the exemplary alleles disclosed herein but include those having at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, and at least 99% identity to an exemplary allele disclosed herein. For purposes of comparison of the characteristics of the CH3-containing molecules of the present invention to those of wild-type human CH3-containing molecules, the wild-type sequences are those set forth in FIG. 8(a) SEQ ID NOS:1-4 (IgG1, IgG2, IgG3, and IgG4, respectively).

It is contemplated that the creation of monomeric Fc-containing molecules is not limited to those based on IgG Fc but are also applicable to the Fc region of other immunoglobulin subclasses including IgA, IgE, IgD, and IgM.

Figure 1:
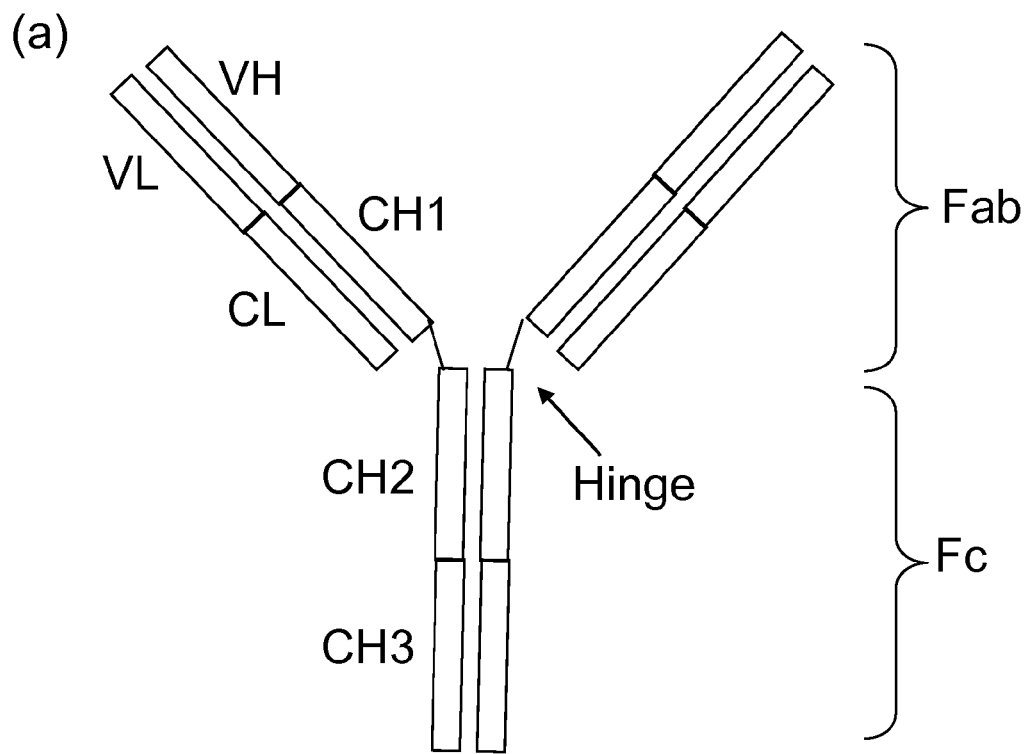
FIG. 1. (a) Schematic diagram of IgG1 antibody with the domains indicated. The IgG1 antibody is a Y-shaped tetramer with two heavy chains (longer length) and two light chains (shorter length). The two heavy chains are linked together by disulfide bonds (—S—S—) at the hinge region. Fab—fragment antigen binding, Fc—fragment crystallizable, VL—variable light chain domain, VH—variable heavy chain domain, CL—constant (no sequence variation) light chain domain, CH1—constant heavy chain domain 1, CH2—constant heavy chain domain 2, CH3—constant heavy chain domain 3. (b) Schematic diagram of monovalent antibody—Fab fused to monomeric Fc. In this case, CH3 domain interface is modified through amino acid mutations.
Figure 1:
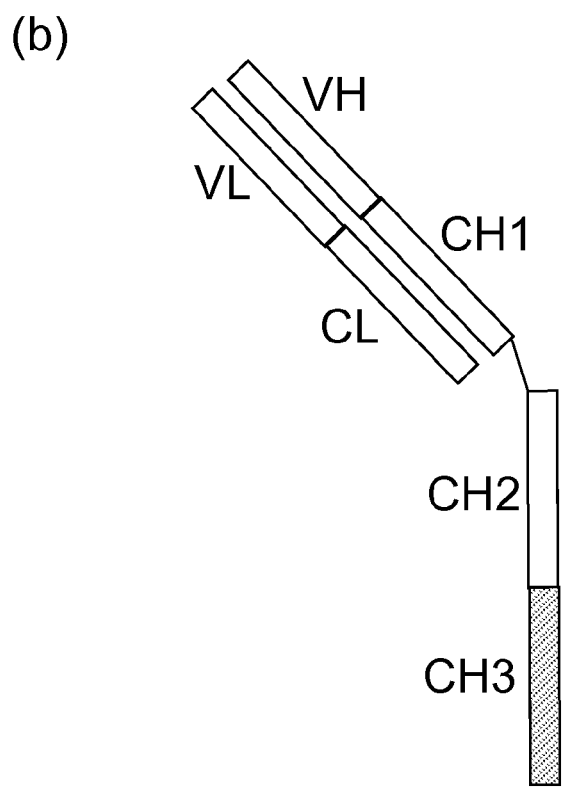
Figure 2:
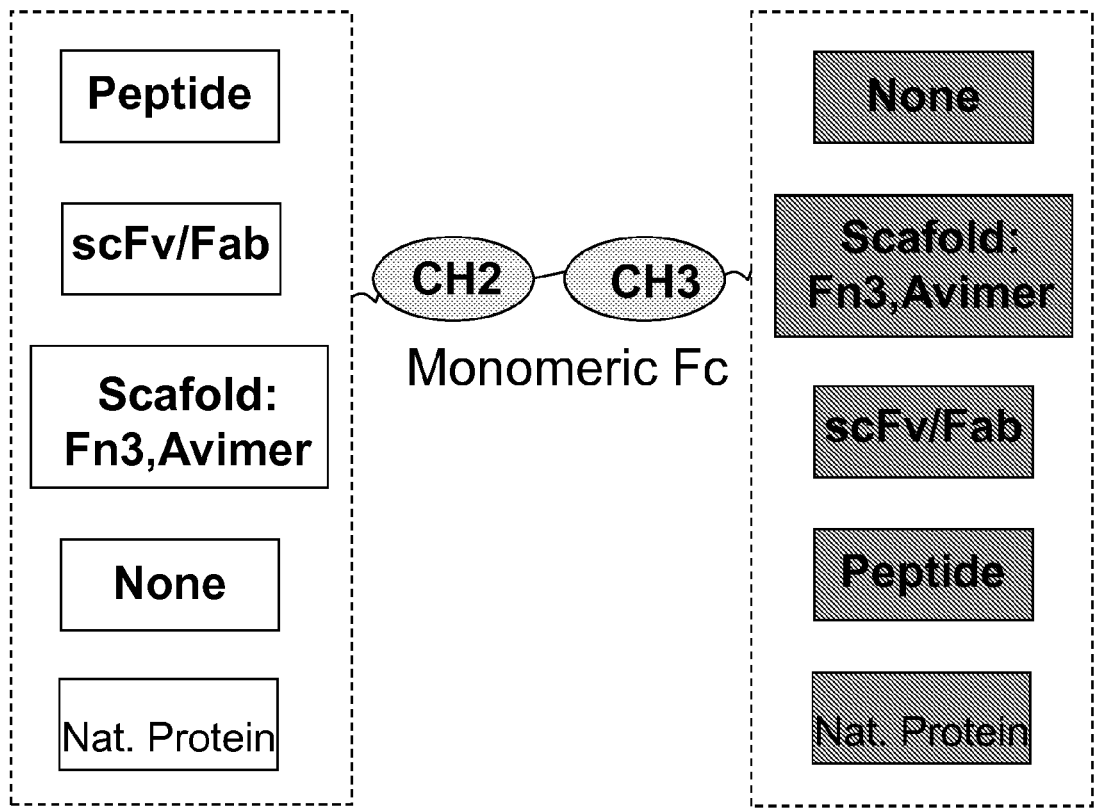
FIG. 2. Figure depicts some of the embodiments that include monomeric (or monovalent) Fc. These include fusion to both N and C terminus of the monomeric Fc. The Fc retains its ability to interact with the FcRn receptor, even without dimerization or the Fab domains, leading to longer serum half-life for proteins/domains that are fused to the monomeric Fc. scFv—single chain fragment variable domain.
Figure 2:
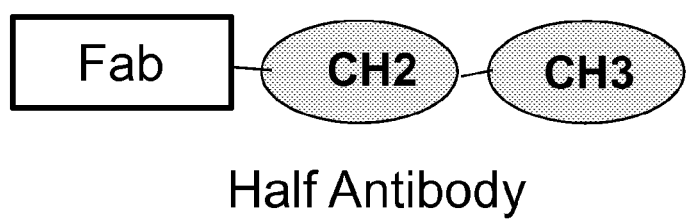

Virtually any molecule that contains an Fc domain may comprise a monomeric Fc domain of the present invention. Examples of such molecules are shown in FIG. 2. As seen in FIG. 2, various peptides may be fused or conjugated to the N-terminus or C-terminus of the Fc. In certain embodiments, the Fc-containing molecule is fused to an Fab to create a half-antibody. Such half-antibody can be created by expressing a heavy chain comprising a monomeric Fc and a light chain recombinantly in a cell, e.g., CHO cell. The heavy chain may contain one or more further mutations. In certain embodiments, the heavy chain further comprises mutation of one or more cysteine residues in the hinge region (Allen et al., *Biochemistry*. 2009 May 5; 48 (17):3755-66).

The Fc polypeptides of the present invention demonstrate reduced dimerization as compared to wild-type Fc molecules. Thus, embodiments of the invention include compositions comprising an antibody or Fc-fusion molecule wherein the amount of Fc-Fc dimerization exhibited by said antibody or Fc-fusion molecule is less than 15%, less than 14%, less than 13%, less than 12%, less than 11%, less than 10%, less than 9%, less than 8%, less than 7%, less than 6%, less than 5%, less than 4%, less than 3%, less than 2%, or less than 1%. Dimerization may be measured by a number of techniques known in the art. Preferred methods of measuring dimerization include Size Exclusion Chromatography (SEC), Analytical Ultra Centrifugation (AUC), Dynamic Light Scattering (DLS), and Native PAGE.

The Fc monomer molecules described herein are useful for extending half-life of therapeutic proteins or domains. Diseases that may be treated with an Fc monomer therapeutic may include inflammation, cancer, metabolic disorders, and others. Potential fusion targets include natural protein binding domains (such as IL-1Ra, TIMP3, SHK peptide, EPO, G-CSF), antibody fragments (such as Fab, scFv, diabody, variable domain derived binders), alternative scaffold derived protein binding domains (such as Fn3 variants, ankyrin repeat variants, centyrin variants, avimers) and peptides recognizing specific antigens. Fc monomer fusion proteins have the advantage of small in size, therefore potentially better ability to penetrate tissues. Fc monomer fusion proteins can be especially useful when monovalency of target binding is preferred. Such monovalency is often preferred when targeting cell-surface molecules that are susceptible to agonism when targeted using multivalent antibodies.

DEFINITIONS

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

The following terms, unless otherwise indicated, shall be understood to have the following meanings: The term "isolated molecule" (where the molecule is, for example, a polypeptide, a polynucleotide, or an antibody) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

Polynucleotide and polypeptide sequences are indicated using standard one- or three-letter abbreviations. Unless otherwise indicated, polypeptide sequences have their amino termini at the left and their carboxy termini at the right, and single-stranded nucleic acid sequences, and the top strand of double-stranded nucleic acid sequences, have their 5' termini at the left and their 3' termini at the right. A particular polypeptide or polynucleotide sequence also can be described by explaining how it differs from a reference sequence.

The terms "peptide" "polypeptide" and "protein" each refers to a molecule comprising two or more amino acid residues joined to each other by peptide bonds. These terms encompass, e.g., native and artificial proteins, protein fragments and polypeptide analogs (such as muteins, variants, and fusion proteins) of a protein sequence as well as post-translationally, or otherwise covalently or non-covalently, modified proteins. A peptide, polypeptide, or protein may be monomeric or polymeric.

The term "polypeptide fragment" as used herein refers to a polypeptide that has an amino-terminal and/or carboxy-terminal deletion as compared to a corresponding full-length protein. Fragments can be, for example, at least 5, 6, 7, 8, 9, 10, 11, 12, 13, 14, 15, 20, 50, 70, 80, 90, 100, 150, 200, 250, 300, 350, or 400 amino acids in length. Fragments can also be, for example, at most 1,000, 750, 500, 250, 200, 175, 150, 125, 100, 90, 80, 70, 60, 50, 40, 30, 20, 15, 14, 13, 12, 11, or 10 amino acids in length. A fragment can further comprise, at either or both of its ends, one or more additional amino acids, for example, a sequence of amino acids from a different naturally-occurring protein or an artificial amino acid sequence.

Polypeptides of the invention include polypeptides that have been modified in any way and for any reason, for example, to: (1) reduce susceptibility to proteolysis, (2) reduce susceptibility to oxidation, (3) alter binding affinity for forming protein complexes, (4) alter binding affinities, and (4) confer or modify other physicochemical or functional properties. Analogs include muteins of a polypeptide. For example, single or multiple amino acid substitutions (e.g., conservative amino acid substitutions) may be made in the naturally occurring sequence (e.g., in the portion of the polypeptide outside the domain(s) forming intermolecular contacts). A "conservative amino acid substitution" is one that does not substantially change the structural characteristics of the parent sequence (e.g., a replacement amino acid should not tend to break a helix that occurs in the parent sequence, or disrupt other types of secondary structure that characterize the parent sequence or are necessary for its functionality). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. Nature 354:105 (1991), which are each incorporated herein by reference.

A "variant" of a polypeptide comprises an amino acid sequence wherein one or more amino acid residues are inserted into, deleted from and/or substituted into the amino acid sequence relative to another polypeptide sequence. Variants of the invention include those comprising a variant CH2 or CH3 domain. In certain embodiments, a variant comprises one or more mutations that when present in an Fc molecule increase affinity for the polypeptide to one or more FcγRs. Such variants demonstrate enhanced antibody-dependent cell-mediated cytotoxicity. Examples of variants providing such are described in U.S. Pat. No. 7,317,091.

Other variants include those that decrease the ability of CH3-domain containing polypeptides to homodimerize. Examples of such Fc variants are described in U.S. Pat. Nos. 5,731,168 and 7,183,076. Further examples are described in the co-owned U.S. Provisional Applications 61/019,569, filed Jan. 7, 2008, and 61/120,305, filed Dec. 5, 2008 (both incorporated by reference in their entirety).

A "derivative" of a polypeptide is a polypeptide (e.g., an antibody) that has been chemically modified, e.g., via conjugation to another chemical moiety such as, for example, polyethylene glycol, a cytotoxic agent, albumin (e.g., human serum albumin), phosphorylation, and glycosylation. Unless otherwise indicated, the term "antibody" includes, in addition to antibodies comprising two full-length heavy chains and two full-length light chains, derivatives, variants, fragments, and muteins thereof, examples of which are described herein.

The term "human antibody" includes all antibodies that have one or more variable and constant regions derived from human immunoglobulin sequences. In one embodiment, all of the variable and constant domains are derived from human immunoglobulin sequences (a fully human antibody). These antibodies may be prepared in a variety of ways, examples of which are described below, including through the immunization with an antigen of interest of a mouse that is genetically modified to express antibodies derived from human heavy and/or light chain-encoding genes. In certain embodiments, the heavy chain of a human antibody is altered in the CH3 domain to reduce the ability of the heavy chain to dimerize.

A humanized antibody has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. Examples of how to make humanized antibodies may be found in U.S. Pat. Nos. 6,054,297, 5,886,152 and 5,877,293.

The term "chimeric antibody" refers to an antibody that contains one or more regions from one antibody and one or more regions from one or more other antibodies. In one example of a chimeric antibody, a portion of the heavy and/or light chain is identical with, homologous to, or derived from an antibody from a particular species or belonging to a particular antibody class or subclass, while the remainder of the chain(s) is/are identical with, homologous to, or derived from an antibody (-ies) from another species or belonging to another antibody class or subclass. Also included are fragments of such antibodies that exhibit the desired biological activity.

Fragments or analogs of antibodies can be readily prepared by those of ordinary skill in the art following the teachings of this specification and using techniques well-known in the art. Preferred amino- and carboxy-termini of fragments or analogs occur near boundaries of functional domains. Structural and functional domains can be identified by comparison of the nucleotide and/or amino acid sequence data to public or proprietary sequence databases. Computerized comparison methods can be used to identify sequence motifs or predicted protein conformation domains that occur in other proteins of known structure and/or function. Methods to identify protein sequences that fold into a known three-dimensional structure are known. See, e.g., Bowie et al., 1991, Science 253:164.

A "CDR grafted antibody" is an antibody comprising one or more CDRs derived from an antibody of a particular species or isotype and the framework of another antibody of the same or different species or isotype.

The "percent identity" of two polynucleotide or two polypeptide sequences is determined by comparing the sequences using the GAP computer program (a part of the GCG Wisconsin Package, version 10.3 (Accelrys, San Diego, Calif.)) using its default parameters.

The terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding an antibody or an Fc-fusion, and a derivative, mutein, or variant thereof.

Two single-stranded polynucleotides are "the complement" of each other if their sequences can be aligned in an anti-parallel orientation such that every nucleotide in one polynucleotide is opposite its complementary nucleotide in the other polynucleotide, without the introduction of gaps, and without unpaired nucleotides at the 5' or the 3' end of either sequence. A polynucleotide is "complementary" to another polynucleotide if the two polynucleotides can hybridize to one another under moderately stringent conditions. Thus, a polynucleotide can be complementary to another polynucleotide without being its complement.

A "vector" is a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: Methods in Enzymology 185, Academic Press, San Diego, Calif. and Baron et al., 1995, Nucleic Acids Res. 23:3605-06.

A "host cell" is a cell that can be used to express a nucleic acid, e.g., a nucleic acid of the invention. A host cell can be a prokaryote, for example, E. coli, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Exemplary host cells include Chinese hamster ovary (CHO) cell lines or their derivatives including CHO strain DXB-11, which is deficient in DHFR (see Urlaub et al., 1980, Proc. Natl. Acad. Sci. USA 77:4216-20), CHO cell lines which grow in serum-free media (see Rasmussen et al., 1998, Cytotechnology 28:31), CS-9 cells, a derivative of DXB-11 CHO cells, and AM-1/D cells (described in U.S. Pat. No. 6,210,924). Other CHO cells lines include CHO-K1 (ATCC# CCL-61), EM9 (ATCC# CRL-1861), and UV20 (ATCC# CRL-1862). Examples of other host cells include COS-7 line of monkey kidney cells (ATCC CRL 1651) (see Gluzman et al., 1981, Cell 23:175), L cells, C127 cells, 3T3 cells (ATCC CCL 163), HeLa cells, BHK (ATCC CRL 10) cell lines, the CV1/EBNA cell line derived from the African green monkey kidney cell line CV1 (ATCC CCL 70) (see McMahan et al., 1991, EMBO J. 10:2821), human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Typically, a host cell is a cultured cell that can be transformed or transfected with a polypeptide-encoding nucleic acid, which can then be expressed in the host cell.

The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but to the progeny or potential progeny of such a cell. Because certain modifications may occur in succeeding generations due to, e.g., mutation or environmental influence, such progeny may not, in fact, be identical to the parent cell, but are still included within the scope of the term as used herein.

Pharmaceutical Compositions

The polypeptides of the invention are particularly useful for formulation into pharmaceutical compositions. Such compositions comprise one or more additional components such as a physiologically acceptable carrier, excipient or diluent. Optionally, the composition additionally comprises one or more physiologically active agents, for example, as described below. In various particular embodiments, the composition comprises one, two, three, four, five, or six physiologically active agents in addition to one or more monomeric antibody and/or Fc-fusion protein of the present invention.

In one embodiment, the pharmaceutical composition comprises a monomeric antibody and/or Fc-fusion protein of the invention together with one or more substances selected from the group consisting of a buffer, an antioxidant such as ascorbic acid, a low molecular weight polypeptide (such as those having fewer than 10 amino acids), a protein, an amino acid, a carbohydrate such as glucose, sucrose or dextrins, a chelating agent such as EDTA, glutathione, a stabilizer, and an excipient. Neutral buffered saline or saline mixed with conspecific serum albumin are examples of appropriate diluents. In accordance with appropriate industry standards, preservatives such as benzyl alcohol may also be added. The composition may be formulated as a lyophilizate using appropriate excipient solutions (e.g., sucrose) as diluents. Suitable components are nontoxic to recipients at the dosages and concentrations employed. Further examples of components that may be employed in pharmaceutical formulations are presented in Remington's Pharmaceutical Sciences, 16th Ed. (1980) and 20th Ed. (2000), Mack Publishing Company, Easton, Pa.

Kits for use by medical practitioners are provided including one or more monomeric antibody and/or Fc-fusion proteins of the invention and a label or other instructions for use in treating any of the conditions discussed herein. In one embodiment, the kit includes a sterile preparation of one or more monomeric antibody and/or Fc-fusion protein, which may be in the form of a composition as disclosed above, and may be in one or more vials.

Dosages and the frequency of administration may vary according to such factors as the route of administration, the particular monomeric antibody and/or Fc-fusion protein employed, the nature and severity of the disease to be treated, whether the condition is acute or chronic, and the size and general condition of the subject. Appropriate dosages can be determined by procedures known in the pertinent art, e.g. in clinical trials that may involve dose escalation studies.

A monomeric antibody and/or Fc-fusion protein of the invention may be administered, for example, once or more than once, e.g., at regular intervals over a period of time. In particular embodiments, a monomeric antibody and/or Fc-fusion protein is administered over a period of at least once a month or more, e.g., for one, two, or three months or even indefinitely. For treating chronic conditions, long-term treatment is generally most effective. However, for treating acute conditions, administration for shorter periods, e.g. from one to six weeks, may be sufficient. In general, the monomeric antibody and/or Fc-fusion protein is administered until the patient manifests a medically relevant degree of improvement over baseline for the chosen indicator or indicators.

As is understood in the pertinent field, pharmaceutical compositions comprising the monomeric antibody and/or Fc-fusion protein of the invention are administered to a subject in a manner appropriate to the indication. Pharmaceutical compositions may be administered by any suitable technique, including but not limited to parenterally, topically, or by inhalation. If injected, the pharmaceutical composition can be administered, for example, via intra-articular, intravenous, intramuscular, intralesional, intraperitoneal or subcutaneous routes, by bolus injection, or continuous infusion. Localized administration, e.g. at a site of disease or injury is contemplated, as are transdermal delivery and sustained release from implants. Delivery by inhalation includes, for example, nasal or oral inhalation, use of a nebulizer, inhalation of the monomeric antibody and/or Fc-fusion protein in aerosol form, and the like.

EXAMPLES

Example 1

The residues involved in the CH3-CH3 domain interaction were identified using a distance limit criterion. There were twenty four residues located at the CH3 domain interface (Table 1). These twenty four residues were examined for side chain structural conservation using available known Fc antibody crystal structures (FIG. 3). The analysis revealed high structural conservation for some of the hydrophobic residues. Free energy of association between the two CH3 domains was also calculated using a computational method (Pokala and Handel 2005) by mutating the 24 interface positions and L398 (a residue in contact with the interface residue K392) with Alanine, one residue at a time. The calculation and the structural conservation analysis revealed that 6 out of the 24 residues contributed significantly to the CH3 domain dimer formation. These 6 positions were analyzed to determine the effect of substitution.

TABLE 1

List of CH3 domain interface residues in the first chain (A) and their side chain contacting residues in the second chain (B)[a]

| Interface Res. in Chain A | Side Chain Contacting Residues in Chain B |
|---|---|
| GLN A 347 | LYS B 360' |
| TYR A 349 | SER B 354' ASP B 356' GLU B 357' LYS B 360' |
| THR A 350 | SER B 354' ARG B 355' |
| LEU A 351 | LEU B 351' PRO B 352' PRO B 353' SER B 354' THR B 366' |
| SER A 354 | TYR B 349' THR B 350' LEU B 351' |
| ARG A 355 | THR B 350' |
| ASP A 356 | TYR B 349' LYS B 439' |
| GLU A 357 | TYR B 349' LYS B 370' |
| LYS A 360 | GLN B 347' TYR B 349' |
| SER A 364 | LEU B 368' LYS B 370' |
| THR A 366 | LEU B 351' TYR B 407' |
| LEU A 368 | SER B 364' LYS B 409' |
| LYS A 370 | GLU B 357' SER B 364' |
| ASN A 390 | SER B 400' |
| LYS A 392 | LEU B 398' ASP B 399' SER B 400' PHE B 405' |
| THR A 394 | THR B 394' VAL B 397' PHE B 405' TYR B 407' |
| PRO A 395 | VAL B 397' |
| VAL A 397 | THR B 393' THR B 394' PRO B 395' |
| ASP A 399 | LYS B 392' LYS B 409' |
| SER A 400 | ASN B 390' LYS B 392' |
| PHE A 405 | LYS B 392' THR B 394' LYS B 409' |
| TYR A 407 | THR B 366' THR B 394' TYR B 407' SER B 408' LYS B 409' |
| LYS A 409 | LEU B 368' ASP B 399' PHE B 405' TYR B 407' |
| LYS A 439 | ASP B 356' |

[a]Due to the 2-fold symmetry present in the CH3-CH3 domain interaction, each pair-wise interaction is represented twice in the structure (for example, Ser A 364 - Leu B 368' & Leu A 439 - Ser B 364'). However, Leu A 351 - Pro B 352', Leu A 351 - Pro B 353', Lys A 392 - Leu B 398', Val A 397 - Thr B 393', and Tyr A 407 - Ser B 408' pairs involve sidechain - mainchain contacts, so they are represented once only.

Fc mutant proteins corresponding to Threonine substitution at each of the 6 positions were generated (Table 2). Additionally, F405T Y407R and Y407R Fc mutants were also generated. To enhance the likelihood of complete monomeric Fc formation, mutations at the 6 positions were generated in the background of a CH3/CH3 weakening Fc variant, in which Lysine 392 and Lysine 409 are mutated to Aspartic acid (K392D K409D Fc).

TABLE 2

| construct | mutations in huIgG1Fc | MW by SEC | AUC |
|---|---|---|---|
| 1 | K392D-K409D | 59,000 | Dimer/Monomer |
| 2 | K392DK409D-Y349T | 36,600 | Monomer |
| 3 | K392DK409D-L351T | 38,000 | ND |
| 4 | K392DK409D-L368T | 33,600 | ND |
| 5 | K392DK409D-L398T | 57,800 | ND |
| 6 | K392DK409DF405T | 38,800 | Dimer/Monomer |
| 7 | K392DK409D-Y407T | 48,200; 41,100 | ND |
| 8 | K392DK409D-F405T-Y407R | 57,800; 41,200 | ND |
| 9 | K392DK409D-Y407R | 65,400 | ND |

ND; not determined.

Mutations listed in Table 2 (#2 to #9) in human IgG1 Fc K392D K409D were generated using Multi-QuikChange site directed mutagenesis (Strategene). Oligo primers used are as follows:

```
                                      (SEQ ID NO: 10)
2:  5'- gaaccacaggtgactaccctgccccatc (SEQ ID NO: 11)
3:  5'- caggtgtacaccactcccccatcccggg (SEQ ID NO: 12)
4:  5'- cagcctgacctgcactgtcaaaggcttctatc (SEQ ID NO: 13)
5:  5'- cacgcctcccgtgactgactccgacggctc (SEQ ID NO: 14)
6:  5'- gacggctccttcactctctatagcgac (SEQ ID NO: 15)
7:  5'- ctccttcttcctcactagcgacctcacc (SEQ ID NO: 16)
8:  5'- gacggctccttcactctccgaagcgacctcacc (SEQ ID NO: 17)
9:  5'- ctccttcttcctccgaagcgacctcacc
```

Expected mutations were confirmed by DNA sequencing. The parental (hu IgG1 Fc K409D K392D) and mutant Fc proteins were expressed in 293E cell using a pTT5 transient mammalian expression vector. The Fc proteins were purified using standard protein A chromatography (5 ml column, Pierce). Fc protein homogeneity analysis (SEC) was performed using a TOSO46mm SW3000 column (TOSO Biosciences LLC, PA). Protein concentrations were determined by measuring the absorption at 280 nm and calculation using 1 mg/ml=1.74 $OD_{280}$.

In each sample case, 5 ug of protein is treated with non-reducing SDS or reducing SDS sample buffer (Invitrogen), run on 4-20% TG gel (Invitrogen) and stained with Gel-code reagent (Pierce).

BIAcore analysis of human and mouse FcRn binding to Fc mutant #1 (Fc K392D-K409D, dimer), #2 (Fc K392D-K409D-Y349T, monomeric SEC profile) and #6 (Fc K392D-K409D-Y349T, monomeric SEC profile) using a BIAcore3000 instrument. CHO cell produced huFc was immobilized on follow cell 2 (Fc2) on a CM5 chip. Fc1 was used as background control. 2 nM human FcRn were incubated with 1, 10, 100 nM of indicated Fc variants for one hour before injected to the CHO huFc surface. Reduced binding of FcRn to the immobilized CHO huFc indicates binding of FcRn to the Fc variants in solution. 2 nM mouse FcRn were incubated with 0.1, 1, 10 nM of Fc variants for one hour before injected to the CHO huFc surface.

Protein concentrations for mutant Fc were 0.4 and 0.6 mg/ml, respectively. Samples in PBS were analyzed by a Beckmann Coulter ProteomeLab XL-1 instrument. The sedimentation velocity experiments were performed at 50,000 rpm followed by absorbance at 280 nm in double-sector centerpiece cell assemblies with quartz windows. Scans were collected at 20° C. without delay between them. The AUC-SV data were analyzed using SEDFIT version 9.4. In the AUC-SV analysis the frictional ration, time invariant noise, and meniscus values were allowed to float during the non-linear least square fit.

Example 2

This Example demonstrates the PK parameters of monomer Fc constructs of various molecular weights in normal mice. The Monomer Fc comprised the K392D-K409D-Y349T mutations. Monomer Fc N297A comprised the Monomer Fc having a further mutation at N297 to remove a glycosylation site. Half IgG comprised a Fab fused to the Monmeric Fc. Fab FnFn comprised the Fab fused to a fibronectin dimer. Fab His was the Fab fused to a histidine tag. huFc WT deltaH comprised a WT Fc dimer minus the hinge region. Fifty four SCID mice were assigned to the following treatment groups. All mice were dosed 10 mg/kg IV and serum was collected at 0.25, 2, 4, 8, 20 and 32 hours.

TABLE 3

| Group | Subgroup | Mouse | Compound | Rou | Dose | Serum Collection |
|---|---|---|---|---|---|---|
| 1 | A | 1-3 | Monomer Fc | IV | 10 mg/kg | 0.25 hrs, 8 hrs |
|   | B | 4-6 |  |  |  | 2 hrs, 20 hrs |
|   | C | 7-9 |  |  |  | 4 hrs, 32 hrs |
| 2 | A | 10-12 | huFc WT deltaH | IV | 10 mg/kg | 0.25 hrs, 8 hrs |
|   | B | 13-14 |  |  |  | 2 hrs, 20 hrs |
|   | C | 16-18 |  |  |  | 4 hrs, 32 hrs |
| 3 | A | 19-21 | Half IgG | IV | 10 mg/kg | 0.25 hrs, 8 hrs |
|   | B | 22-24 |  |  |  | 2 hrs, 20 hrs |
|   | C | 25-27 |  |  |  | 4 hrs, 32 hrs |
| 4 | A | 28-30 | Fab FnFn | IV | 10 mg/kg | 0.25 hrs, 8 hrs |
|   | B | 31-33 |  |  |  | 2 hrs, 20 hrs |
|   | C | 34-36 |  |  |  | 4 hrs, 32 hrs |
| 5 | A | 37-39 | Fab-His | IV | 10 mg/kg | 0.25 hrs, 8 hrs |
|   | B | 40-42 |  |  |  | 2 hrs, 20 hrs |
|   | C | 43-45 |  |  |  | 4 hrs, 32 hrs |
| 6 | A | 46-48 | Monomer Fc N297A | IV | 10 mg/kg | 0.25 hrs, 8 hrs |
|   | B | 49-51 |  |  |  | 2 hrs, 20 hrs |
|   | C | 52-54 |  |  |  | 4 hrs, 32 hrs |

Analytical Method Summary:

For quantitation of monomer Fc contructs. a microtiter plate (Maxisorp, Nunc) was coated with either goat anti-human IgG Fcγ specific (Jackson Cat #109-005-098) for Groups 1, 2 and 6 or goat anti-human IgG F(ab')$_2$ specific (Jackson Cat #109-005-097) for Groups 3, 4 and 5. After blocking with 10% NFDM (Nonfat Dry Milk) in PBST, standards, quality control samples (QCs), and test samples were incubated after pretreatment at a dilution factor of 50 in NFDM/PBST. Unbound constructs were removed by washing with PBST buffer. Next, horseradish peroxidase-labelled goat anti-human IgG Fcγ specific (Jackson Cat #109-035-098) was added to detect captured Fc constructs in Groups 1, 2 and 6 whereas goat anti-human IgG F(ab')$_2$ specific (Jackson Cat #109-036-097) was used to detect captured F(ab')$_2$ constructs in Groups 3, 4 and 5. After a final wash step, TMB substrate solution (1:1 tetramethylbenzidine and peroxide, Kirkegaard & Perry Laboratories) was added and quenched with phosphoric acid. Optical densities (ODs) were determined at a wavelength of 450-650 nm. The conversion of OD values into concentrations for the QCs and unknown specimens was achieved through Watson software mediated comparison to a concurrently analyzed standard curve, which was regressed according to a four-parameter logistic model.

TABLE 4

Data for Serum Specimens

| GROUP | TREATMENT | HOURS | Subgroup A NG/ML | Subgroup B NG/ML | Subgroup C NG/ML |
|---|---|---|---|---|---|
| 1 | MONFC | 0.25 | 15200 | 24300 | 20300 |
| 1 | MONFC | 2 | 2170 | 2630 | 1880 |
| 1 | MONFC | 4 | 1160 | 862 | 748 |
| 1 | MONFC | 8 | 282 | 360 | 382 |
| 1 | MONFC | 20 | 131 | 142 | 121 |
| 1 | MONFC | 32 | 98.6 | 89.2 | 82.1 |
| 2 | HUFCWT | 0.25 | 126000 | 243000 | 71200 |
| 2 | HUFCWT | 2 | 60000 | 54100 | 63900 |
| 2 | HUFCWT | 4 | 44700 | 67200 | 43900 |
| 2 | HUFCWT | 8 | 30500 | 34300 | 24400 |
| 2 | HUFCWT | 20 | 25600 | 25200 | 19900 |
| 2 | HUFCWT | 32 | 18600 | 18900 | 15900 |
| 3 | HALF IgG | 0.25 | 89200 | 103000 | 98400 |
| 3 | HALF IgG | 2 | 42600 | 39200 | 41400 |
| 3 | HALF IgG | 4 | 24900 | 28200 | 21900 |
| 3 | HALF IgG | 8 | 11400 | 9880 | 11500 |
| 3 | HALF IgG | 20 | 2290 | 1930 | 2090 |
| 3 | HALF IgG | 32 | 1070 | 1060 | 1270 |
| 4 | FNFN | 0.25 | 95400 | 89900 | 101000 |
| 4 | FNFN | 2 | 7300 | 5460 | 9600 |
| 4 | FNFN | 4 | 3060 | 3490 | 3440 |
| 4 | FNFN | 8 | 1010 | 1010 | 1070 |
| 4 | FNFN | 20 | 172 | 171 | 181 |
| 4 | FNFN | 32 | 43.6 | 50.3 | 54.6 |
| 5 | FAB-HIS | 0.25 | 55300 | 70000 | 87900 |
| 5 | FAB-HIS | 2 | 3190 | 3240 | 3250 |
| 5 | FAB-HIS | 4 | 1380 | 1480 | 1520 |
| 5 | FAB-HIS | 8 | 502 | 575 | 604 |
| 5 | FAB-HIS | 20 | 72.5 | 71.1 | 82.6 |
| 5 | FAB-HIS | 32 | 0 | 0 | 0 |
| 6 | N297A | 0.25 | 51200 | 52800 | 59400 |
| 6 | N297A | 2 | 784 | 1010 | 911 |
| 6 | N297A | 4 | 368 | 392 | 397 |
| 6 | N297A | 8 | 213 | 250 | 222 |
| 6 | N297A | 20 | 118 | 105 | 104 |
| 6 | N297A | 32 | 78.5 | 77.4 | 64.3 |

AQL > 125,000 ng/mL BQL < 50 ng/mL

TABLE 5

|  | Monomer Fc | huFc WT delta H | Half-IgG | FabFn dimer | Fab-His | Monomer Fc N297A |
|---|---|---|---|---|---|---|
| AUC (ug * hr/mL) | 25.9 | 983 | 342 | 97.4 | 58.4 | 35.1 |
| T½ (hrs) | 9 | 21 | 6.3 | 4.8 | 3.8 | 12.1 |
| CL (mL/min/kg) | 6.16 | 0.109 | 0.473 | 1.71 | 2.83 | 4.58 |
| Molecular Weight (approx) | 25 kDa | 50 kDa | 70 kDa | 70 kDa | 50 kDa | 25 kDa |

This Example demonstrates the normal mouse PK parameters, i.e. the extent of FcRn interactions, of monomer Fc constructs of various molecular weights above or below the kidney clearance threshold of ~60 KDa. The huFC WT delta H construct which consists of a dimer CH2-CH3 domain demonstrated the greatest exposure/AUC compared to all other constructs despite its molecular weight below the clearance threshold. The Half IgG molecule, which consists of a Fab Fc Monomer, demonstrated 35% of the exposure of the dimer Fc but had 3.5-fold greater AUC compared to the size-matched Fab Fn dimer, which consists of a Fab-fibronectin dimer, a result that demonstrated the role of Fc in increasing half-life and ultimately exposure. The Fab alone and the monomer Fc constructs, either WT or N297A variant which lacks glycosylation due to the removal of the N-linked addition site, all demonstrated rapid clearance and minimal AUC values of 17 to 38-fold less than the huFC WT delta H construct.

REFERENCES

Bahar, I. and R. L. Jernigan (1997). "Inter-residue potentials in globular proteins and the dominance of highly specific hydrophilic interactions at close separation." J Mol Biol 266 (1): 195-214.

Bernstein, F. C., T. F. Koetzle, et al. (1977). "The Protein Data Bank: a computer-based archival file for macromolecular structures." J Mol Biol 112 (3): 535-42.

Deisenhofer, J. (1981). "Crystallographic refinement and atomic models of a human Fc fragment and its complex with fragment B of protein A from *Staphylococcus aureus* at 2.9- and 2.8-A resolution." Biochemistry 20 (9): 2361-70.

Ghetie, V. and E. S. Ward (2000). "Multiple roles for the major histocompatibility complex class I-related receptor FcRn." Annu Rev Immunol 18: 739-66.

Huber, R. (1984). "Three-dimensional structure of antibodies." Behring Inst Mitt (76): 1-14.

Idusogie, E. E., L. G. Presta, et al. (2000). "Mapping of the C1q binding site on rituxan, a chimeric antibody with a human IgG1 Fc." J Immunol 164 (8): 4178-84.

Lee, B. and F. M. Richards (1971). "The interpretation of protein structures: estimation of static accessibility." J Mol Biol 55 (3): 379-400.

Martin, W. L., A. P. West, Jr., et al. (2001). "Crystal structure at 2.8 A of an FcRn/heterodimeric Fc complex: mechanism of pH-dependent binding." Mol Cell 7 (4): 867-77.

Papadea, C. and I. J. Check (1989). "Human immunoglobulin G and immunoglobulin G subclasses: biochemical, genetic, and clinical aspects." Crit. Rev Clin Lab Sci 27 (1): 27-58.

Pokala, N. and T. M. Handel (2005). "Energy functions for protein design: adjustment with protein-protein complex affinities, models for the unfolded state, and negative design of solubility and specificity." J Mol Biol 347 (1): 203-27.

Roux, K. H. (1999). "Immunoglobulin structure and function as revealed by electron microscopy." Int Arch Allergy Immunol 120(2): 85-99.

Ye, Y. and A. Godzik (2004). "FATCAT: a web server for flexible structure comparison and structure similarity searching." Nucleic Acids Res 32 (Web Server issue): W582-5.

What is claimed:

1. A polypeptide comprising a monomeric Fc region having a CH2 and CH3 domain, wherein said CH3 domain is an IgG CH3 domain and comprises:
   (a) a negatively charged amino acid at EU position 392 and EU position 409; and
   (b) an amino acid substitution of EU position 349 or EU position 405 with a polar amino acid residue.

2. The polypeptide of claim 1, wherein the polar amino acid residue is threonine.

3. The polypeptide of claim 1, wherein the CH3 domain is a human IgG CH3 domain.

4. The polypeptide of claim 1, wherein EU position Y349 is substituted with a polar amino acid residue.

5. The polypeptide of claim 4, wherein threonine is substituted for Y349.

6. The polypeptide of claim 1, wherein the negatively charged amino acid is aspartic acid.

7. The polypeptide of claim 1, wherein said polypeptide comprises an antibody variable domain.

8. The polypeptide of claim 7, wherein said polypeptide comprises a CH1 domain.

9. The polypeptide of claim 8, wherein said polypeptide comprises an antibody heavy chain.

10. A monomeric antibody comprising the antibody heavy chain of claim 9 and an antibody light chain.

* * * * *